(12) United States Patent
Washburn

(10) Patent No.: US 10,054,577 B2
(45) Date of Patent: Aug. 21, 2018

(54) METHOD AND SYSTEM FOR OBTAINING GEOCHEMISTRY INFORMATION FROM PYROLYSIS INDUCED BY LASER INDUCED BREAKDOWN SPECTROSCOPY

(71) Applicant: Ingrain, Inc., Houston, TX (US)

(72) Inventor: Kathryn Elizabeth Washburn, Houston, TX (US)

(73) Assignee: Ingrain, Inc., Houston, TX (US)

( * ) Notice: Subject to any disclaimer, the term of this patent is extended or adjusted under 35 U.S.C. 154(b) by 0 days.

(21) Appl. No.: 14/827,358

(22) Filed: Aug. 17, 2015

(65) Prior Publication Data

US 2016/0054284 A1 Feb. 25, 2016

Related U.S. Application Data

(60) Provisional application No. 62/150,860, filed on Apr. 22, 2015, provisional application No. 62/038,950, filed on Aug. 19, 2014.

(51) Int. Cl.
*G01N 33/24* (2006.01)
*G01J 3/44* (2006.01)
*G01N 21/71* (2006.01)
*G01J 3/443* (2006.01)

(52) U.S. Cl.
CPC ............ *G01N 33/241* (2013.01); *G01J 3/443* (2013.01); *G01N 21/718* (2013.01); *G01N 2201/06113* (2013.01)

(58) Field of Classification Search
None
See application file for complete search history.

(56) References Cited

U.S. PATENT DOCUMENTS

| 8,081,796 B2 | 12/2011 | Derzhi et al. |
| 8,170,799 B2 | 5/2012 | Dvorkin et al. |
| 2001/0030981 A1* | 10/2001 | Scaggs ............... G01N 21/718 372/9 |

(Continued)

FOREIGN PATENT DOCUMENTS

| WO | 2004/003595 A1 | 1/2004 |
| WO | 2013/023299 A1 | 2/2013 |
| WO | 2013/071188 A1 | 5/2013 |

OTHER PUBLICATIONS

Fortes, F. J., et al. "Spectrochemical study for the in situ detection of oil spill residues using laser-induced breakdown spectroscopy." Analytica chimica acta 683.1 (2010): 52-57.*

(Continued)

*Primary Examiner* — Shawn DeCenzo
(74) *Attorney, Agent, or Firm* — Chamberlain Hrdlicka

(57) ABSTRACT

A method for determining geochemistry of at least one geological sample with laser-induced breakdown spectral measurements performed on the geological sample in a time variant manner with spectral acquisitions made after each of a plurality of measurement shots, spectral pre-processing performed as necessary, and subsequent analysis is applied to the collected data to determine at least one geochemistry parameter of the sample. The method can provide a rapid method to estimate thermal maturity of a sample, which does not require sample preparation, and which can be non-destructive with respect to portions of the sample. A system for performing the method also is provided.

17 Claims, 24 Drawing Sheets

(56) References Cited

U.S. PATENT DOCUMENTS

| | | | |
|---|---|---|---|
| 2014/0204378 A1* | 7/2014 | Day | G01J 3/2823 356/326 |
| 2015/0323516 A1 | 11/2015 | Washburn | |
| 2015/0323517 A1 | 11/2015 | Washburn | |

OTHER PUBLICATIONS

Margetic, V., K. Niemax, and R. Hergenröder. "A study of non-linear calibration graphs for brass with femtosecond laser-induced breakdown spectroscopy." Spectrochimica Acta Part B: Atomic Spectroscopy 56.6 (2001): 1003-1010.*

Cunat, J., et al. "Portable instrument and analytical method using laser-induced breakdown spectrometry for in situ characterization of speleothems in karstic caves." Journal of Analytical Atomic Spectrometry 20.4 (2005): 295-300.*

International Search Report and Written Opinion issued in corresponding International Patent Application No. PCT/US2015/045451 dated Jan. 4, 2016 (15 pages).

Koujelev et al., "Artificial Neural Networks for Material Identification, Mineralogy and Analytical Geochemistry Based on Laser-Induced Breakdown Spectroscopy," Artificial Neural Networks—Industrial and Control Engineering Applications, Intech, Apr. 4, 2011, pp. 91-116.

Lalanne et al., "How to Cope with some of the Challenges Associated with Laboratory Measurements on Gas Shale Core Samples," SPE 167709, SPE/EAGE European Unconventional Conference and Exhibition, Vienna, Austria, Feb. 25-27, 2014 (17 pages).

Nordeng, "Evaluating Source Rock Maturity Using Multi-Sample Kinetic Parameters from the Bakken Formation (Miss.-Dev.), Williston Basin, ND," Geol. Investig. No. 164, North Dak. Geol. Survey, 2013, pp. 1-19 (19 pages).

Peters, "Guidelines for Evaluating Petroleum Source Rock Using Programmed Pyrolysis," The American Associatio of Petroleum Geologist Bulletin, V. 70, No. 3, Mar. 1986, pp. 318-329 (12 pages).

Bellucci et al., "A detailed geochemical investigation of post-nuclear detonation trinitite glass at high spatial resolution: Delineating anthropogenic vs. natural components," Chemical Geology 365, 2014, pp. 69-86 (18 pages).

Tiwari et al., "Detailed Kinetic Analysis of Oil Shale Pyrolysis TGA Data," AIChE Journal, Feb. 2012, vol. 58, No. 2 DOI 10.1002/aic, pp. 505-515 (11 pages).

Lalanne et al., "Benefits of High-Resolution Core Logs Integration in Characterizing Gas Shales Cores", International Symposium of the Society of Core Analysts, SCA Paper No. 2013-076, Sep. 2013 (6 pages).

Grader et al., "Computations of Porosity and Permeability of Sparic Carbonate Using Multi-Scale CT Images," International Symposium of the Society of Core Analysts, SCA2009-Temp Paper #03-10, Sep. 27-30, 2009, pp. 1-10.

* cited by examiner

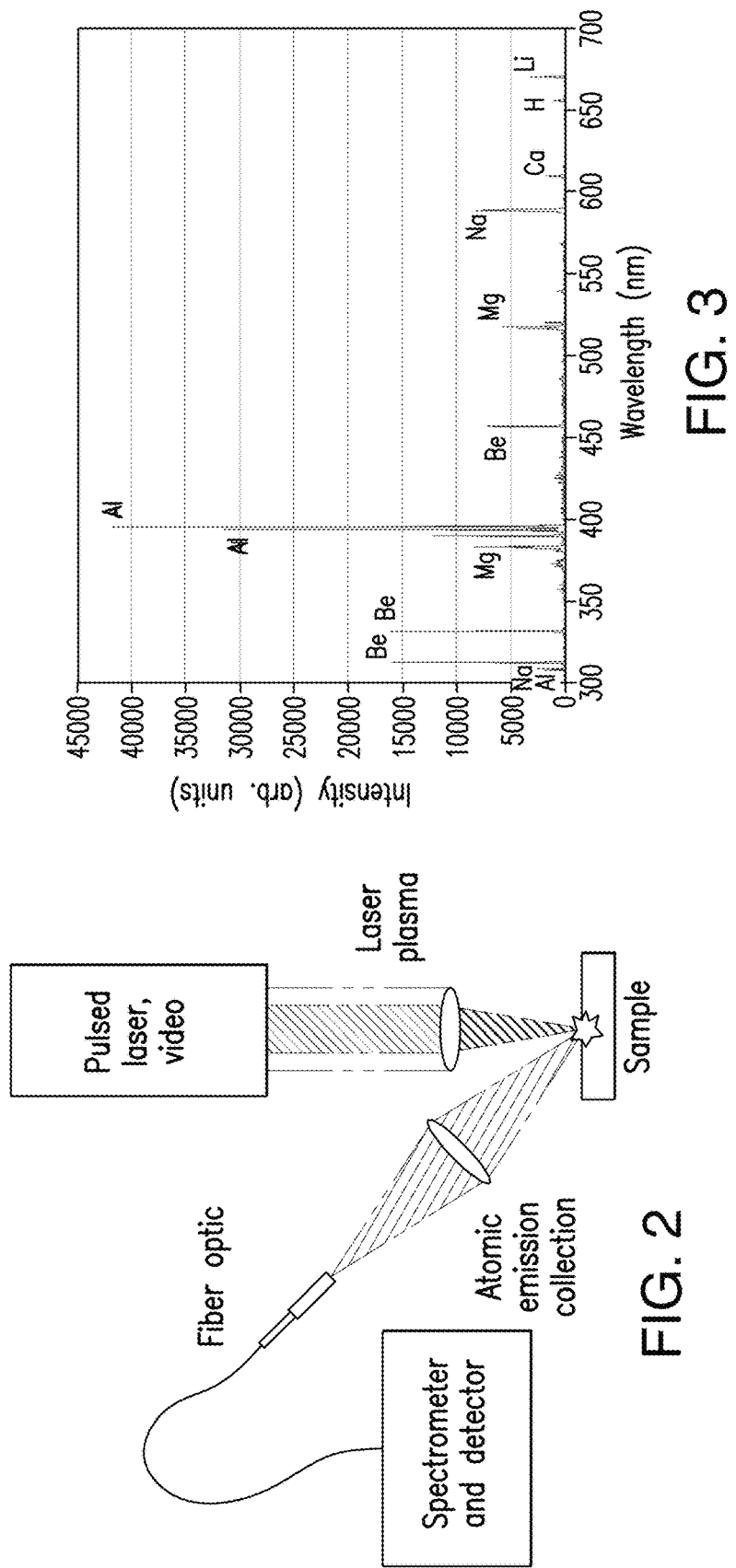

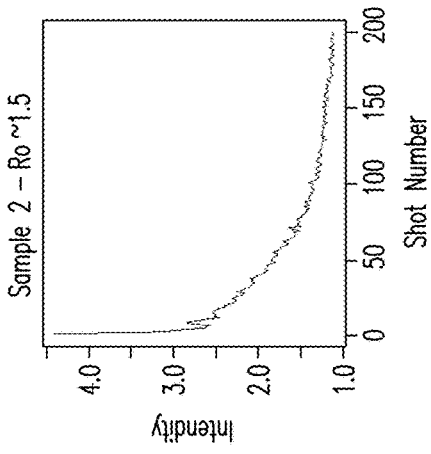
FIG. 13A
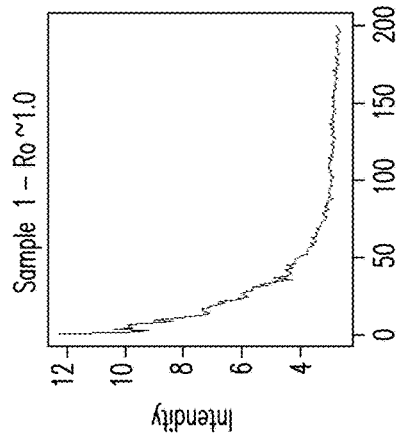
FIG. 13B
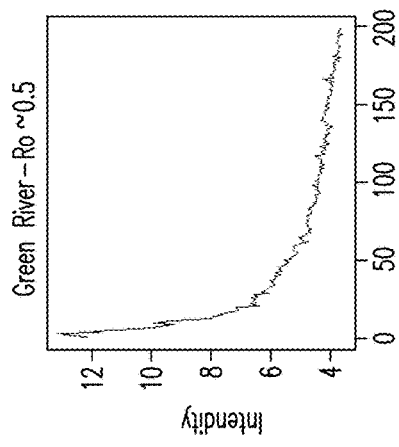
FIG. 13C
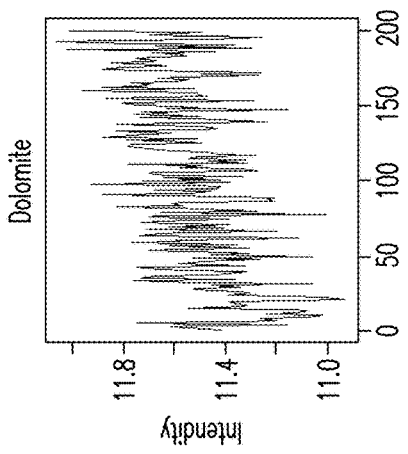
FIG. 13D
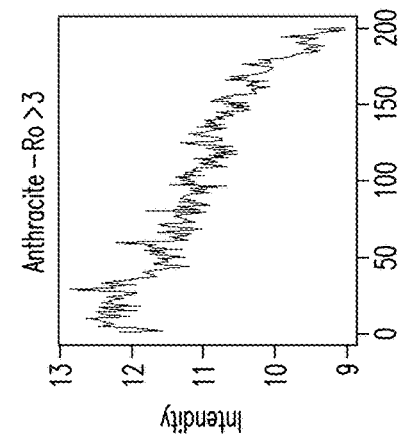
FIG. 13E
FIG. 13F

METHOD AND SYSTEM FOR OBTAINING GEOCHEMISTRY INFORMATION FROM PYROLYSIS INDUCED BY LASER INDUCED BREAKDOWN SPECTROSCOPY

This application claims the benefit under 35 U.S.C. § 119(e) of prior U.S. Provisional Patent Application No. 62/038,950, filed Aug. 19, 2014 and U.S. Provisional Patent Application No. 62/150,860, filed Apr. 22, 2015, which are incorporated in their entirety by reference herein.

FIELD OF THE INVENTION

The present invention relates to a method for obtaining geochemistry information on geological samples or other types of samples and, more particularly, to a method for obtaining geochemistry information on geological materials with laser induced breakdown spectroscopy (LIBS). The present invention also relates to systems for the methods.

BACKGROUND OF THE INVENTION

Characterisation of source rocks is important for evaluation of both conventional and unconventional reservoirs. Organic matter is deposited and preserved at the bottom of lakes, seas and deltas. As more material is deposited, the organic matter is buried and the heat and pressure of burial transforms the organic matter into geopolymers such as kerogen and bitumen. When the rocks containing organic matter are buried deep enough, the rocks undergo catagenesis, where temperature begins to convert the kerogen into bitumen and ultimately into hydrocarbons such as oil and gas. The rocks that produce hydrocarbons are referred to as source rocks.

Kerogen and bitumen are large organic molecules of no fixed structure. The composition of the kerogen and bitumen depends both on the type of organic matter used to produce them and the thermal maturity of the sample. While kerogen and bitumen have different molecular structures, they are typically separated functionally; the latter is soluble in common organic solvents while the former is not. The majority of bitumen is produced later during catagenesis, though a small amount occurs from diagenesis.

Understanding kerogen and bitumen properties and content is important for estimation of thermal maturity and potential hydrocarbon production. Thermal maturity indicates how much and what type of hydrocarbon is expected to be produced from an unconventional shale reservoir or a conventional reservoir sourced by a particular or multiple source rocks. In addition to kerogen and bitumen, a third class of organic matter, pyrobitumen, may exist in more thermally mature systems. Like kerogen, pyrobitumen is also insoluble in typical organic solvents. However, while kerogen originates from the originally deposited organic matter, the pyrobitumen comes from the cracking of bitumen during catagenesis and metagenesis.

The current standard method for determining thermal maturity is programmed pyrolysis, such as the "Rock-Eval™" (Vinci Technologies) or "Source Rock Analysis" techniques. These will heat up a crushed portion of sample in an oven or ovens in a series of stages at different temperatures to pyrolyse and oxidize the sample. The "Rock-Eval™" analyser, for example, includes a flame ionization detector (FID) that measures organic compound gases released during each stage of heating while sensitive infrared detectors are used to measure the quantity of CO and $CO_2$ generated during pyrolysis and oxidation of samples. A thermocouple monitors temperatures, which are recorded on a chart known as a pyrogram. The measured organic compound gases, CO and $CO_2$ are plotted as a function of temperature on the pyrogram. During the first heating stage, the sample is held at an initial temperature for a period of time and the produced organic products are measured. This is referred to as the S1 peak, which relates to the hydrocarbons and bitumen in the sample. The temperature is then ramped higher at a set heating rate. A second peak, S2, corresponds to the hydrocarbons that evolve from the sample during the second programmed heating stage of pyrolysis, which result from the thermal cracking of kerogen. The associated release of carbon dioxide ($CO_2$) and carbon monoxide (CO) during pyrolysis is measured by the IR detector. The S3 peak corresponds to the amount of CO and $CO_2$ that is evolved from thermal cracking of the kerogen during pyrolysis. This peak is associated with the organic associated oxygen in the sample. The temperature at which the S2 peak has the highest signal intensity, and thus maximum generation of hydrocarbons from kerogen, is referred to as Tmax. Tmax relates to thermal maturity, as higher temperatures are required to crack the kerogen into hydrocarbons for more thermally mature samples. There is the potential to heat the sample up to even higher temperatures and observe the produced organic products. For example, the high temperature programmed pyrolysis can be used to measure the $S_{py}$ peak, which relates to pyrobitumen.

The programmed pyrolysis methods are bulk methods; the samples need to be crushed and homogenized before measurement. Therefore, any spatial information regarding the distribution of organic matter is lost during the crushing process. They are also, practically, completely destructive with respect to the samples, as the samples cannot be used for further tests after programmed pyrolysis. Programmed pyrolysis measurements are time intensive, usually requiring about an hour per sample to perform. The results also can have issues with interference from carbonate in the sample. If the samples are carbonate rich, they typically will need to be pretreated with hydrochloric acid to prevent interference in the measurement.

Thermal maturity is often estimated using the temperature where the maximum number of hydrocarbon products are produced from kerogen. This can be unreliable, as the Tmax peaks are often quite broad, such that the exact location of the peak can vary and can be difficult to reproduce with subsequent measurements. Thermal maturity calculations from Tmax are often unreliable particularly for low organic content samples. As programmed pyrolysis methods take approximately an hour per sample, this is a time intensive method to measure thermal maturity.

Fourier Transform Infrared (FTIR) spectroscopy has been used to estimate these parameters. Analysis of the FTIR spectrum with multivariate analysis has shown good predictive value for geochemical parameters such as S1, S2, and to a lesser degree S3. Predictive ability of FTIR to date for hydrogen and oxygen indices, however, has been of poor quality. FTIR suffers the same drawback of loss of spatial resolution of the organic matter as the programmed pyrolysis, as samples need to be powdered before measurement.

Laser induced breakdown spectroscopy (LIBS) uses a laser to ablate a tiny portion of sample. The standard for LIBS uses a q-switched solid state laser that produces a rapid pulse, typically on the order of pico- to nanoseconds in duration. Optics are used to focus the energy onto a single spot on the sample. The laser ablates a small amount of sample at this spot, turning it into a high temperature plasma. The excited atoms then return to a ground state, giving off light of characteristic frequencies. The spot size vaporized by the laser can range in size from a few microns up to hundreds of microns, allowing a large range of resolution and is dependent on the optics of the system. The signal quality improves with larger spot size, but sacrifices resolution. While a small amount of sample is consumed, the amount is so small that it is considered to be negligible and the technique is considered non-destructive. The wavelength of light from the plasma can be in the 180 to 980 nm region. Detection means may comprise a spectrometer adjusted to a part of the spectral region. The resulting spectra can be analysed by multivariate data analysis to correlate the spectra to concentration of elements. The spectroscopic analysis of the optical emission in LIBS is different from analytical approaches based on mass spectrometry.

LIBS has been used as a method for mineralogy identification, making it an alternative to X-ray Diffraction (XRD) and X-ray Fluorescence (XRF) methods for mineralogical analysis of samples. It has an advantage over XRF for mineralogical identification because it can measure all elements, whereas XRF is unable to detect light elements. LIBS does have a disadvantage in terms of quantification of heavier elements compared to XRF.

Laser Induced Pyrolysis (LIPS) methods have been used previously on geological samples. LIPS relies on mass-spectroscopy methods of detecting and analysing the products of pyrolysis instead of optical emissions spectroscopy. Further, those LIPS methods appear to be limited to just total organic carbon (TOC), and do not appear to present information on thermal maturity or kerogen versus bitumen discrimination.

SUMMARY OF THE INVENTION

A feature of the present invention is a method to provide an improved method for the analysis of a geological material.

A further feature of the present invention is a system for making such determinations.

To achieve these and other advantages and in accordance with the purposes of the present invention, as embodied and broadly described herein, the present invention relates, in part, to a method for analysing a geological sample, comprising subjecting at least one location of the geological sample to a plurality of successive measurement shots of laser light with each measurement shot at least partly vaporising and turning a portion of the sample into plasma to cause spectral emission; detecting the spectral emission after each measurement shot with at least one spectrum detector; optional or as necessary pre-processing collected data from the spectrum detector in order to transform the data into a suitable form for subsequent analysis; analysis of the raw or preprocessed spectra; and determining at least one geochemistry parameter from the LIBS data.

A system for performing this method is also provided.

The present invention further relates to a method for analysing a geological sample, comprising: subjecting at least one location of at least one geological sample to a plurality of successive measurement shots of laser light with each measurement shot at least partly vaporising and turning a portion of said sample into plasma to cause spectral emission, detecting said spectral emission after each said measurement shot with at least one spectral detector, optional or as needed preprocessing collected data from the spectral detector to make it into a suitable form for analysis, and determining a reaction rate constant k for the Arrhenius equation of the at least one sample using at least one of: i) monitoring changes in amounts of elements associated with organic matter and hydrocarbons for a portion of at least one sample that is heated by the laser-induced pyrolysis, ii) collecting and analysing hydrocarbon species produced by pyrolysis of a portion of at least one sample from the laser-induced pyrolysis by a flame ion detector or gas chromatography-mass spectrometry (GC-MS), iii) monitoring the weight of at least one sample during the laser-induced pyrolysis of at least one sample, iv) monitoring the temperature of at least one sample and determining the amount of energy inputted into the portion of the sample by the laser during the laser-induced pyrolysis. The prefactor in the Arrhenius equation may be inputted based on a priori knowledge or solved for based on measurements performed on two or more different heating rates of the sample. The different heating rates may be obtained by one or more combinations of different laser power, laser spot size or laser shot rate. The kinetic analysis can be used to either solve for the activation energy distribution in the sample or the reaction rates given a known input of energy (e.g., inputted laser energy).

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. The features depicted in the figures are not necessarily drawn to scale. Similarly numbered elements in different figures represent similar components unless indicated otherwise.

BRIEF DESCRIPTION OF THE DRAWINGS

FIG. 2 shows a schematic drawing of an apparatus used for spectral emission acquisition according to an example of the present application.

FIG. 3 shows emission peaks for elements at respective wavelengths from a sample according to an example of the present application.

FIG. 13A shows hydrogen spectral line intensities obtained using LIBS as a function of the number of laser shots for a shale rock sample ("Green River—Ro~0.5") according to an example of the present application.

FIG. 13B shows hydrogen spectral line intensities obtained using LIBS as a function of the number of laser shots for a shale rock sample ("Sample 1—Ro~1") according to an example of the present application.

FIG. 13C shows hydrogen spectral line intensities obtained using LIBS as a function of the number of laser shots for a shale rock sample ("Sample 2—Ro~1.5") according to an example of the present application.

FIG. 13D shows hydrogen spectral line intensities obtained using LIBS as a function of the number of laser shots for a shale rock sample ("Sample 3—Ro~2.5") according to an example of the present application.

FIG. 13E shows hydrogen spectral line intensities obtained using LIBS as a function of the number of laser shots for a rock sample ("Anthracite—Ro>3") according to an example of the present application.

FIG. 13F shows hydrogen spectral line intensities obtained using LIBS as a function of the number of laser shots for a rock sample ("Dolomite") according to an example of the present application.

DETAILED DESCRIPTION OF THE INVENTION

Figure 1:
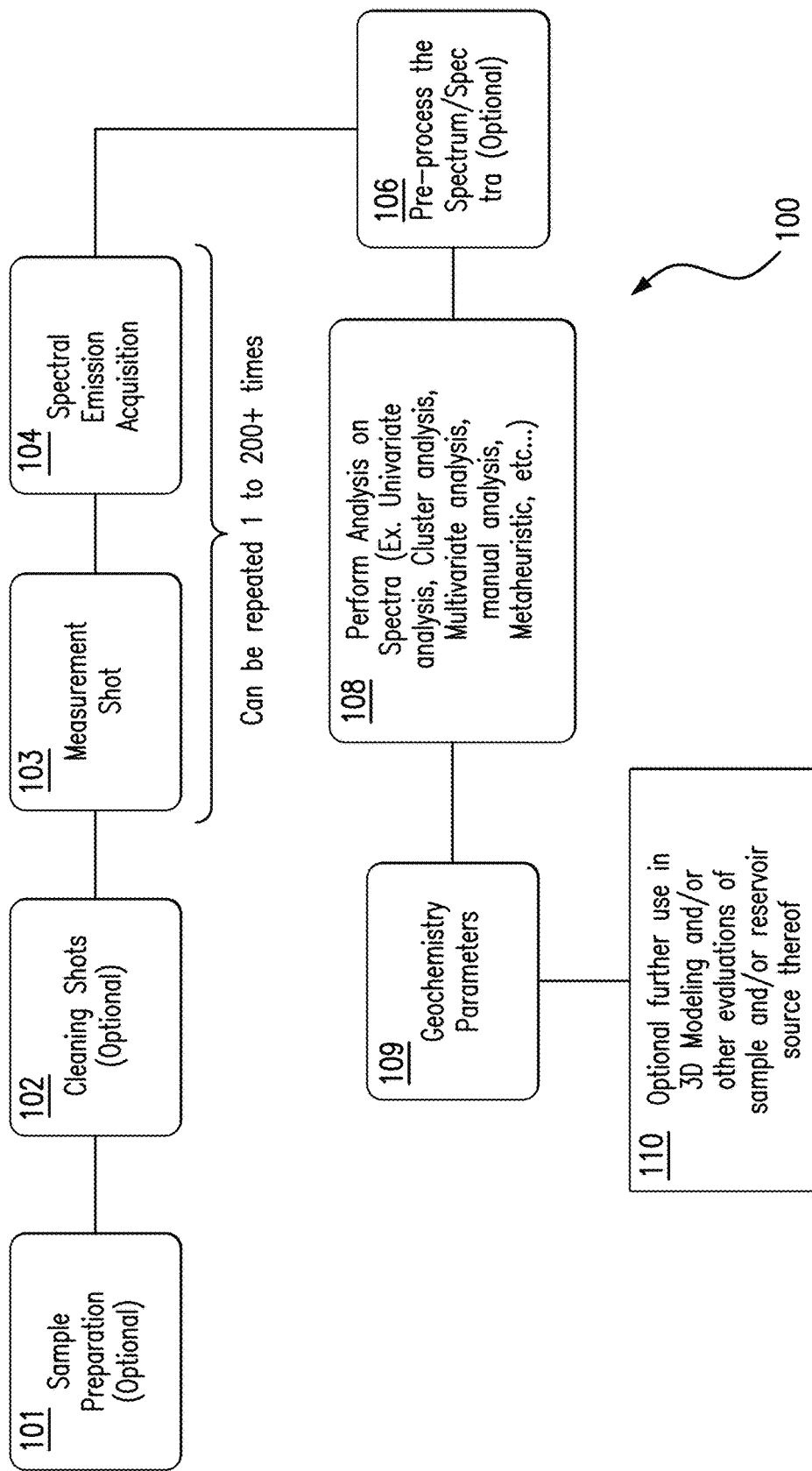
FIG. 1 shows a process flow chart of the determining geochemistry parameters for a sample according to an example of the present application.

The present invention relates in part to a method for determining geochemistry of at least one geological sample with laser-induced breakdown spectral measurements performed on the geological sample in a time variant manner with spectral acquisitions made after each of a plurality of measurement shots, and optional or as needed pre-processing is applied to the collected data from the spectral acquisitions and the raw or pre-processed data is analysed to determine at least one geochemistry parameter of the sample. Though the present invention is illustrated herein with regard to analyses of geological samples, it will be appreciated that the invention may have broader application, such as in metallurgy or other uses.

More specifically, in obtaining spectral data of a sample by LIBS measurements according to a method of the present invention, after cleaning shots, multiple shots of a laser can be performed in rapid succession on the sample to pyrolyse organic matter, wherein a spectral measurement can be taken after each laser pulse, and observation of the loss of elements associated with organic material, typically but not limited to hydrogen, oxygen and carbon, can be observed as the number of laser shots increases. The collected data from the spectral measurements can be pre-processed in order to make the raw data suitable for subsequent analysis to produce one or more geochemical parameters. Pre-processing is a way to take raw data and make it suitable for analysis. For example, pre-processing can be performed by integration of peak area associated with a given element to produce an intensity curve for the element as a function of laser shot number. This can be performed for one or more peaks, either associated with the same element or different elements. The preprocessing can also comprise, for example, analysing the peak maxima associated with an element to produce an intensity curve with laser shot number for one or more elements, sub-selecting actual peak spectra for successive measurement shots, or sub-regions of the spectra or the whole spectra for the successive measurement shots, or compiling the data from the successive laser shots into a matrix, single vector, or other combined form. Pre-processing may also include, but not limited to applying an exponential fitting, bi-exponential fitting, multiple-exponential fitting, an inverse Laplace transform, a Gaussian decay fitting, or other analysis or filter or function to the data, such as taking a derivative, or removing data that do not meet quality control standards. Pre-processing may include a combination of any two or more of these listed steps. Uni-, cluster, multi-variate analysis, neutral nets, self-organising maps, metaheuristic procedures (e.g. particle swarm optimization, genetic algorithms, etc.) or manual analysis can be applied to raw or pre-processed data to produce geochemistry parameters.

The method of the present invention can provide a rapid method to estimate thermal maturity of a sample, such as rapid thermal maturity estimates which can be translated along the length of a core. A more complete elemental set can be provided using the method of the present invention than XRF, with decreased sample preparation time being needed. The method can be non-destructive with respect to most portions of the sample other than the small spot or spots where the laser was impinged. A system for performing the method also is provided.

Further, the geochemistry parameter or parameters determined from the LIBS measurements of the method of the present invention can be used as an input parameter for use in further source or reservoir rock evaluation. The geochemistry parameter or parameters obtained with the present method can be used for three-dimensional analysis of the geological sample. For example, the geochemistry parameters determined by the LIBS measurements can be integrated with spatial information obtained on the same sample to produce three-dimensional models of the geochemistry of the geological sample. The method can allow for kerogen and bitumen to be distinguished in the samples. Spatially resolved maps, for example, can be obtained with the method of the present invention which can be applied to sample models to help distinguish between kerogen and bitumen in the models. Spatially resolved geochemical information can be obtained on the sample by integrating the geochemistry parameters obtained from the indicated LIBS measurements with spatial information obtained on the sample. As another example, the geochemistry parameters determined by the LIBS measurements of the inventive method can be integrated with properties measured by other analytical techniques, such as TOC, S1, S2, S3, $T_{max}$, Ro, HI (hydrogen index), OI (oxygen index), kerogen typing or other properties determined from programmed pyrolysis, and/or from other methods, for further evaluation or modeling of the sample.

FIG. 1 shows a process flow of a method according to an example of the present invention. The method is shown in the figure as process (100), which can include steps 101-110. The sequence of the steps is indicated by the arrows in the figure, and several of the steps can be optional. The method steps are shown as including sample preparation (optional or as needed), cleaning shots (optional or as needed), measurement shot or shots, spectral acquisition, spectral pre-processing (optional or as needed), manual or uni- or cluster or multivariate analysis or neural net or self-organising maps or metaheuristic procedures (e.g. particle swarm optimization, genetic algorithms, etc.) for geochemical parameters attainment, and optional further use of geochemical parameters obtained in further modeling of the geochemistry or characteristics of the sample and/or geological reservoir from which the sample was obtained. Additional details on these various method steps are proved in the descriptions below with further reference made to this and other figures.

The materials, also referred to herein as the samples, to which the present invention can be applied are not necessarily limited. The materials can be geological materials, such as rocks, or samples or subsamples thereof. The kinds of rock to which a method of the present invention can be applied are not necessarily limited. The rock sample can be, for example, organic mud rock, shale, carbonate, sandstone, limestone, dolostone, or other rocks, or any combinations thereof, or other kinds. The rocks can be porous or non-porous. Any source of a rock formation sample of manageable physical size and shape may be used with the present invention. Micro-cores, crushed or broken core pieces, drill cuttings, sidewall cores, outcrop quarrying, whole intact rocks, and the like, may provide suitable rock piece or fragment samples for analysis using methods according to the invention.

LIBS is able to perform depth profiling, firing or pulsing the laser in the same spot and observing the different products that are produced with increased depth. LIBS is also very rapid, only taking seconds per measurement making it amenable for high-throughput industrial use. LIBS measurements can be rastered to produce a two dimensional map of surface composition. When a LIBS measurement is performed on a sample, the laser produces heat that is transferred to the matrix surrounding the shot point. The energy transfer is dependent on the power of the laser, duration of the laser pulse, repetition rate of the laser and the laser spot size. The transfer of energy can lead to volitisation of organic components in the sample in the matrix nearby the laser shot. This loss of organic matter is then detected in the next LIBS measurement. Some components volatise more easily than others. Hydrocarbons and bitumens appear to volatise more rapidly than kerogen, which require more shots of the laser before its loss is detected. Less thermally mature kerogen appears to volatise more easily than more thermally mature kerogen. This is analogous to the programmed pyrolysis measurements, where the kerogen requires higher temperatures than hydrocarbons and bitumens for volitisation and more thermally mature kerogen requires higher temperatures than the immature kerogen.

LIBS is normally performed in a time invariant manner. Frequently a few cleaning shots with the laser are performed in order to remove any unwanted surface contamination. Information from these cleaning shots typically is not saved, but may be. After any cleaning shots, the actual measurements are performed; the laser is used to ablate the sample and the resulting spectral emissions from the produced plasma are recorded. Usually multiple shots are performed. Because there is usually not expected to be any significant changes in the sample with each individual laser shot, the spectral results are commonly added together to improve signal to noise. Other times, each individual spectrum from each laser shot may be recorded, for example if there are expected changes in composition with sample depth. Multiple points on the same sample are frequently sampled in order to confirm repeatability, assess homogeneity and identify any unusual results.

In contrast, LIBS measurements in a method of the present invention are performed in a time variant manner. Unlike LIBS measurements done in a time invariant manner, the time between laser shots is important for the thermal transfer to the surrounding matrix. Low level cleaning shots may be performed in order to remove surface imperfections or contaminants, but a weak power setting typically is used for the cleaning shots in order to avoid pyrolysation of the nearby organic matter. After any cleaning shots, multiple shots of the laser are performed in rapid succession to pyrolyse organic matter. Because a spectral measurement is taken after each laser pulse, observation of the loss of the elements associated with organic material, typically but not limited to hydrogen, oxygen and carbon, can be observed as the number of laser shots increases. The spectral measurement can be based on intensity for a selected spectrum region, or other parameters that can be correlated to elemental content of the sample. Averaging of multiple shots is less likely to be helpful than normal LIBS done in a time invariant manner because of the change in composition with each laser shot. Averaging the signal from measurements at multiple points on the sample may be useful to improve signal to noise and average out heterogeneity in the sample. The total signal loss may be related to the amount of organic matter in the sample and the rate of loss of organic matter to the sample thermal maturity.

Figure 15:
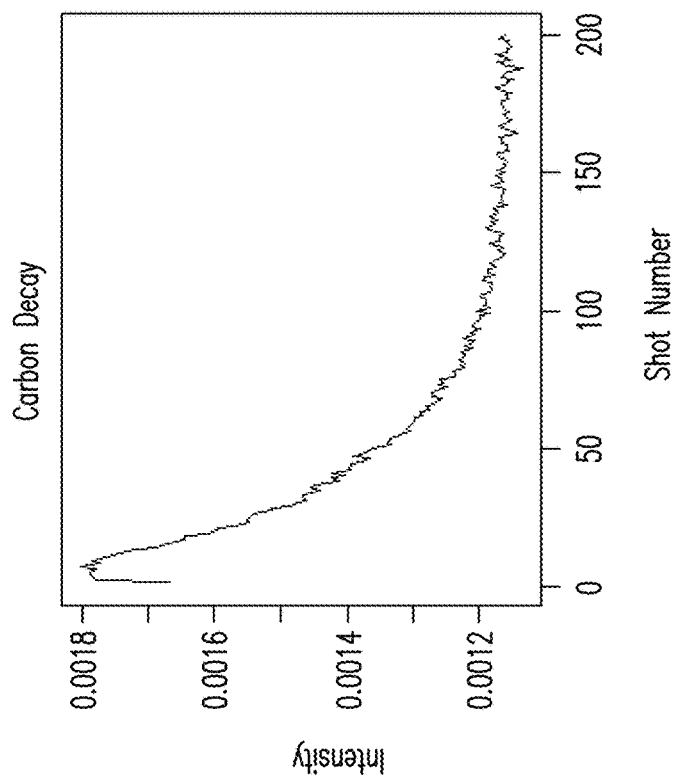
FIG. 15 shows a carbon decay curve with intensity values with respect to the shot number as acquired from LIBS using a method according to an example of the present application.
Figure 14:
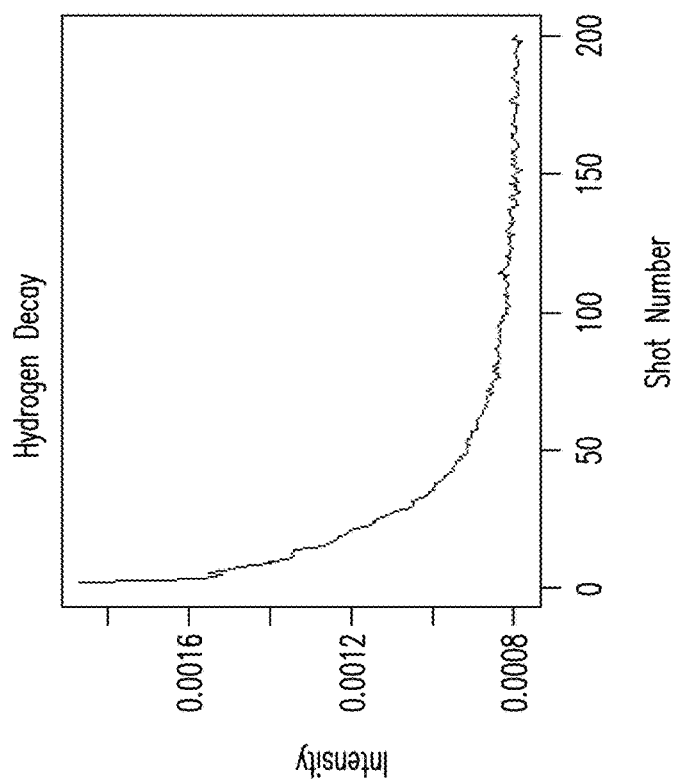
FIG. 14 shows a hydrogen decay curve with intensity values with respect to the shot number as acquired from LIBS using a method according to an example of the present application.
Figure 16:
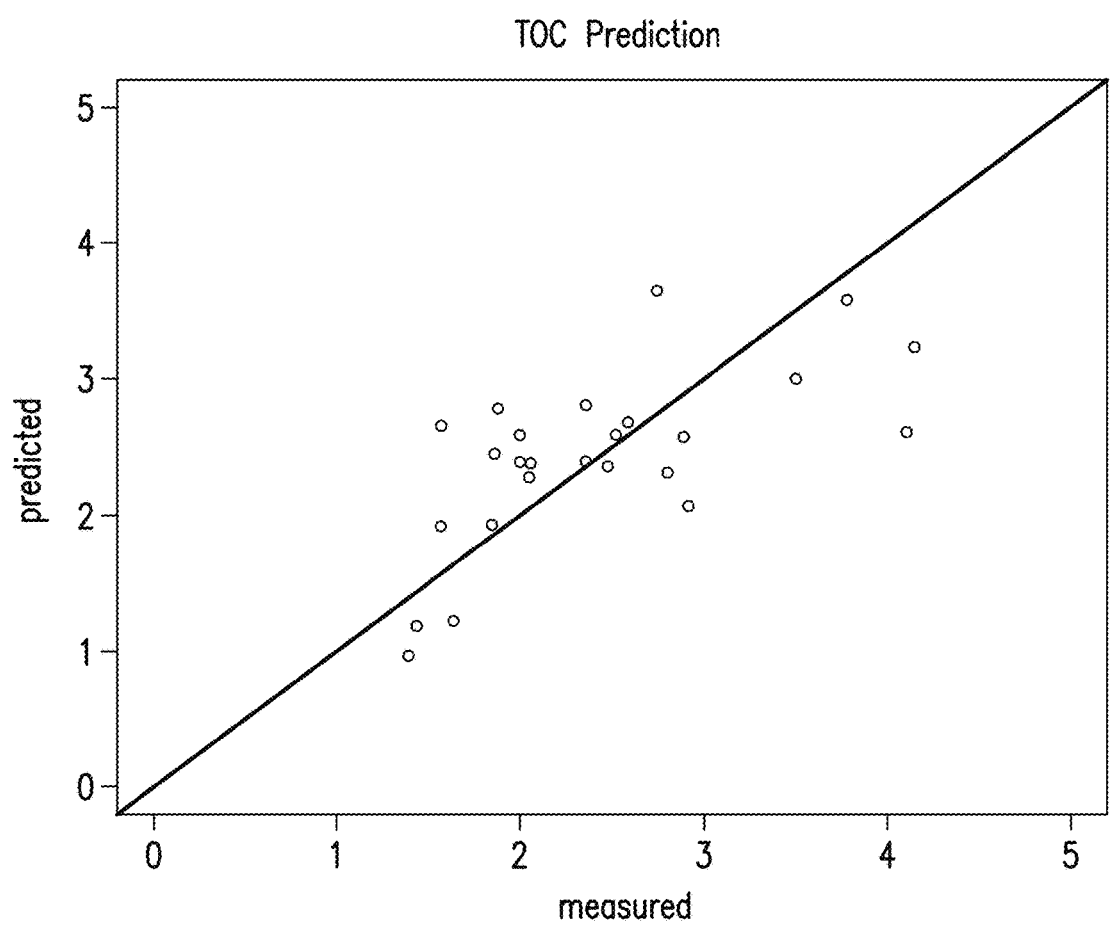
FIG. 16 shows correlation of measured TOC versus predicted TOC from LIBS according to an example of the present application.
Figure 17:
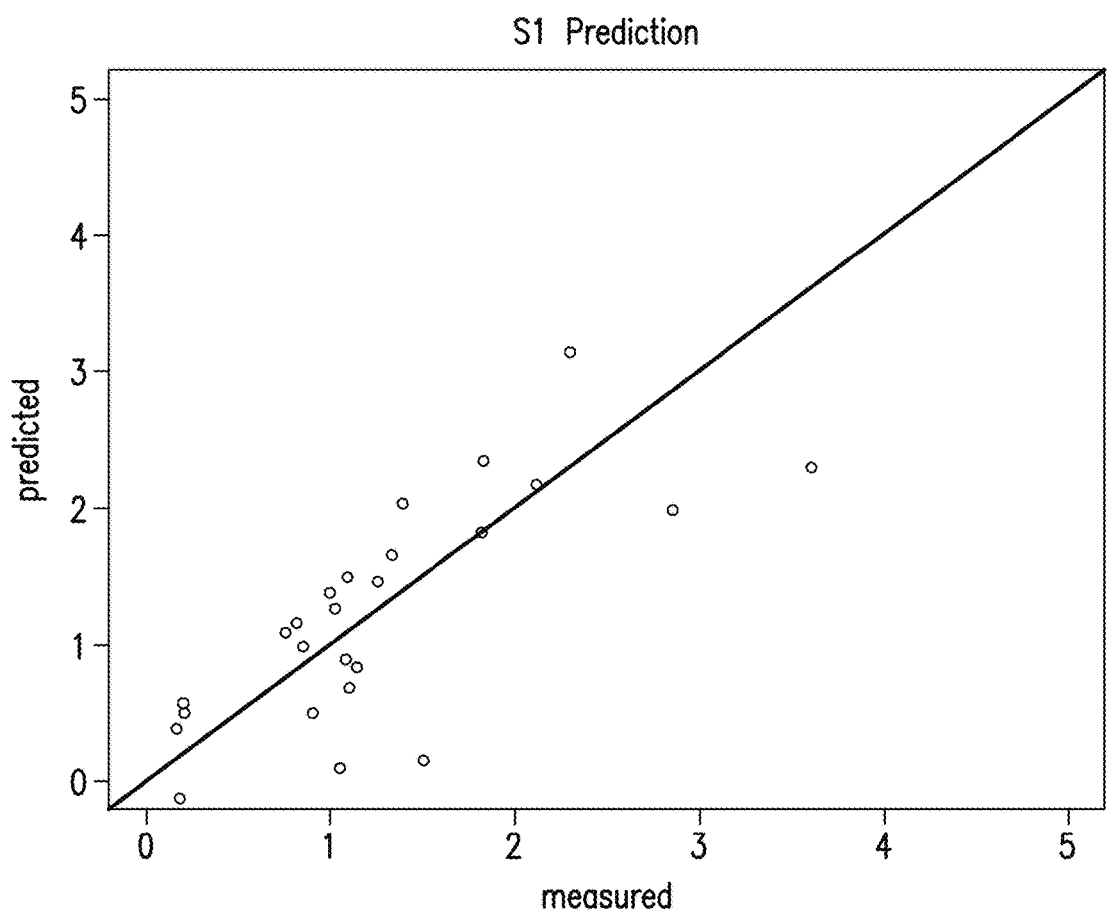
FIG. 17 shows correlation of measured S1 versus predicted S1 from LIBS according to an example of the present application.
Figure 18:
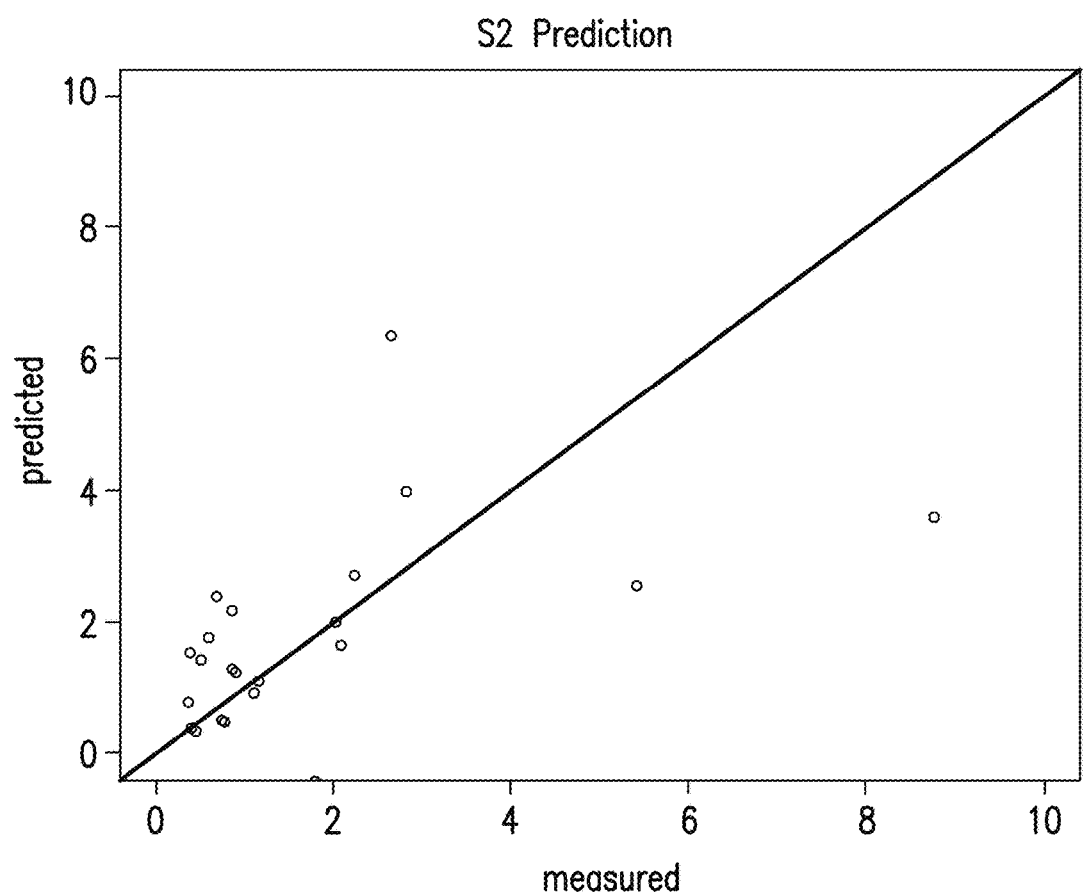
FIG. 18 shows correlation of measured S2 versus predicted S2 from LIBS according to an example of the present application.
Figure 19:
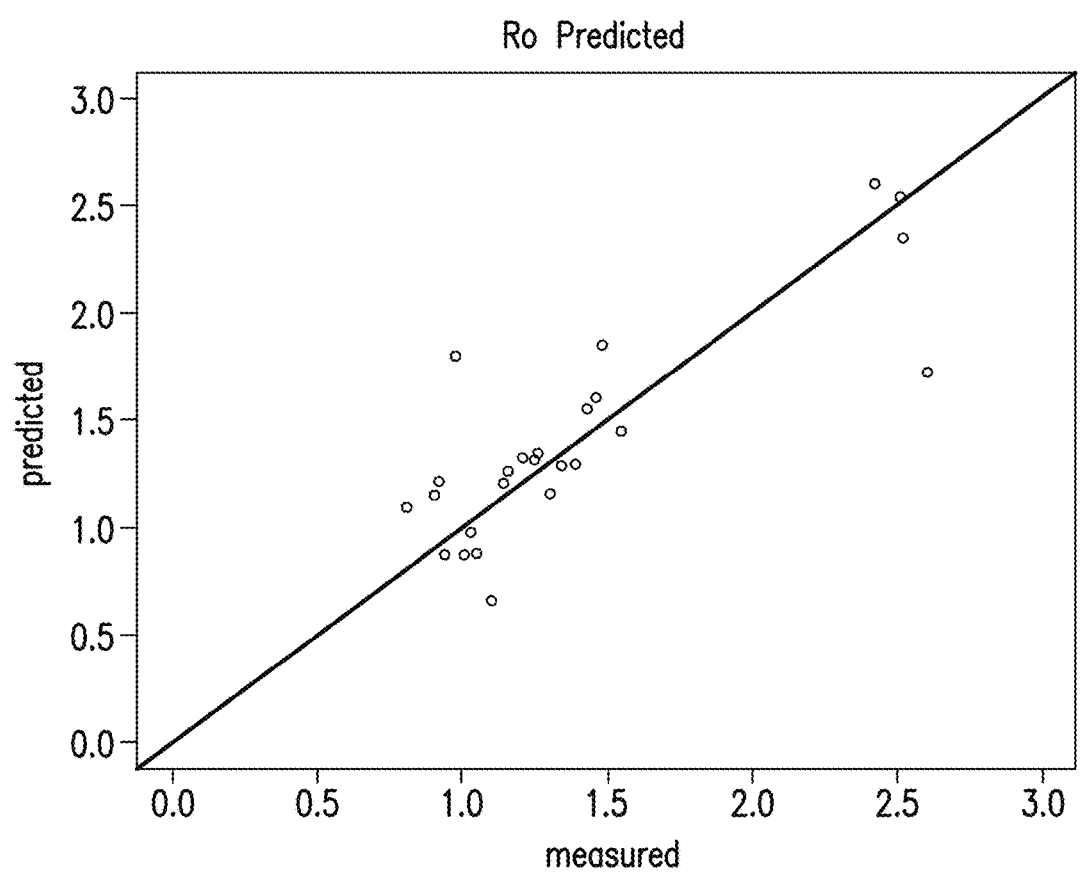
FIG. 19 shows correlation of measured Ro versus predicted Ro from LIBS according to an example of the present application.
Figure 20:
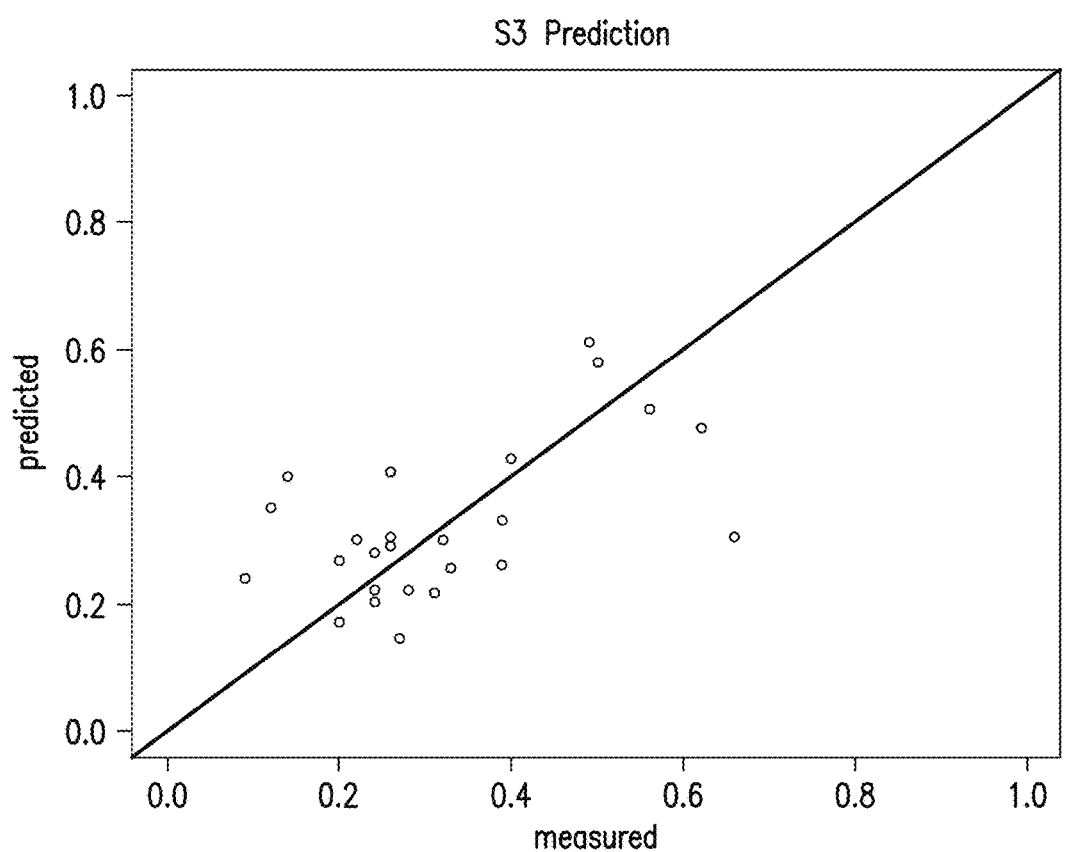
FIG. 20 shows correlation of measured S3 versus predicted S3 from LIBS according to an example of the present application.
Figure 21:
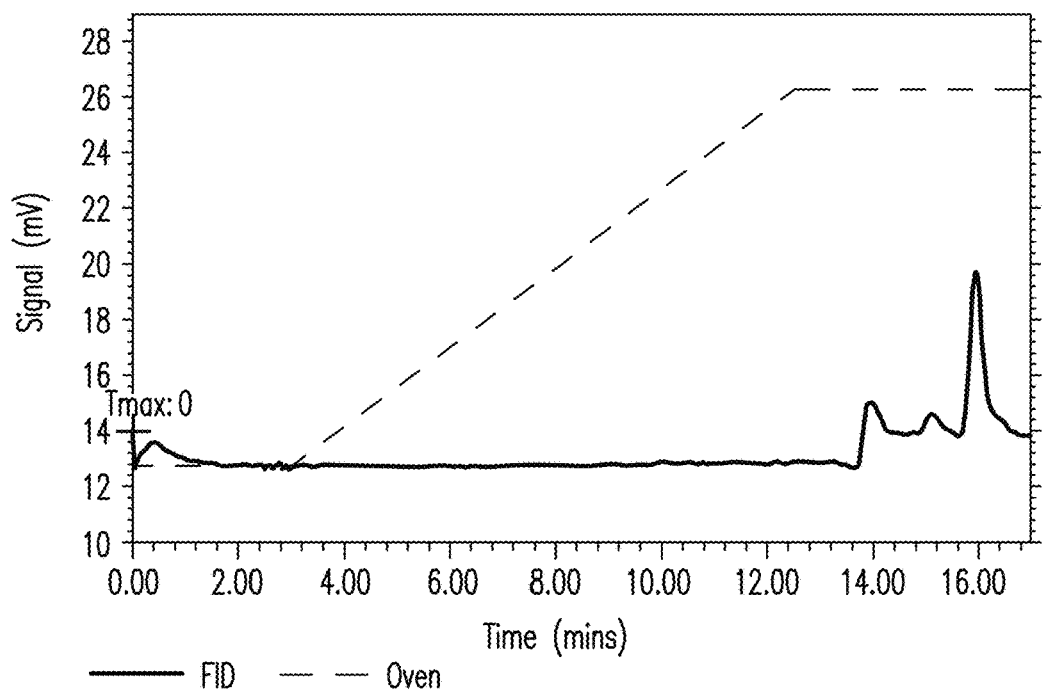
FIG. 21 is a pyrogram obtained by programmed pyrolysis on a thermally mature sample.
Figure 22:
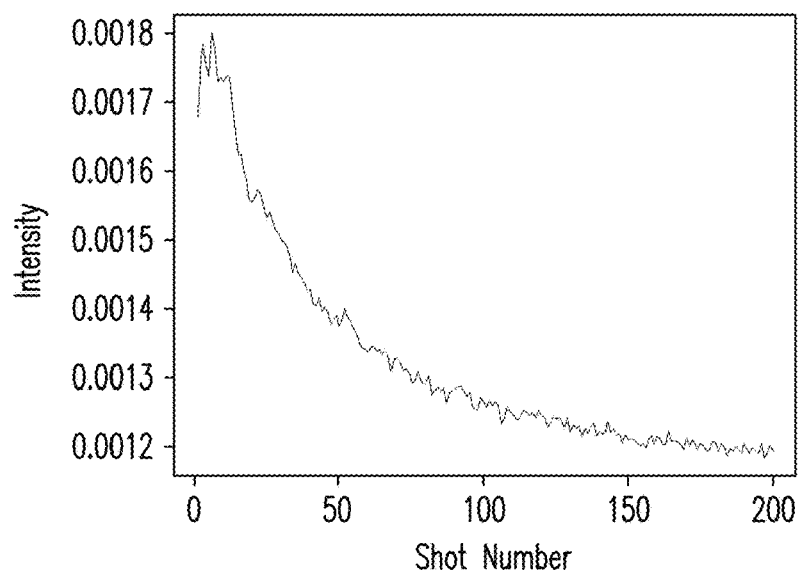
FIG. 22 shows a decay curve with intensity values with respect to the shot number as acquired from LIBS using a method according to an example of the present application for comparison to the results shown in FIG. 21. Whereas the pyrogram in FIG. 21 was unable to determine thermal maturity, the decay curve from LIBS showed behavior consistent with a thermally mature sample (FIGS. 23-24).
Figure 23:
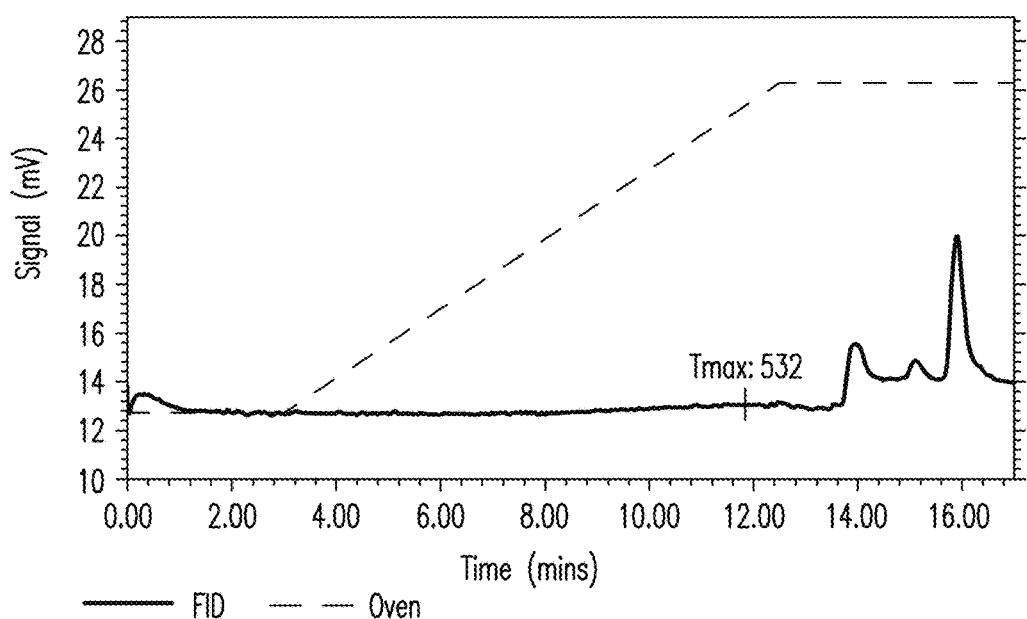
FIG. 23 is a pyrogram obtained by programmed pyrolysis on a thermally mature sample.
Figure 24:
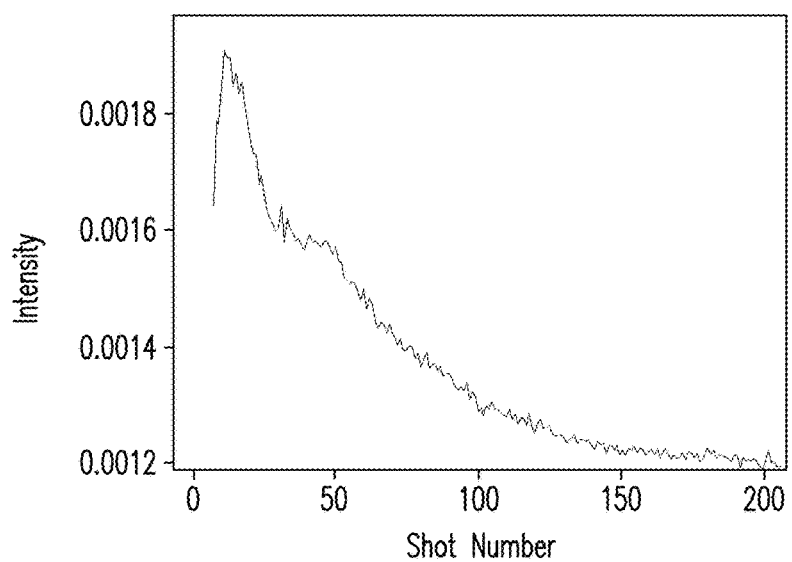
FIG. 24 shows a decay curve with intensity values with respect to the shot number as acquired from LIBS using a method according to an example of the present application for comparison to the results shown in FIG. 23.
Figure 25:
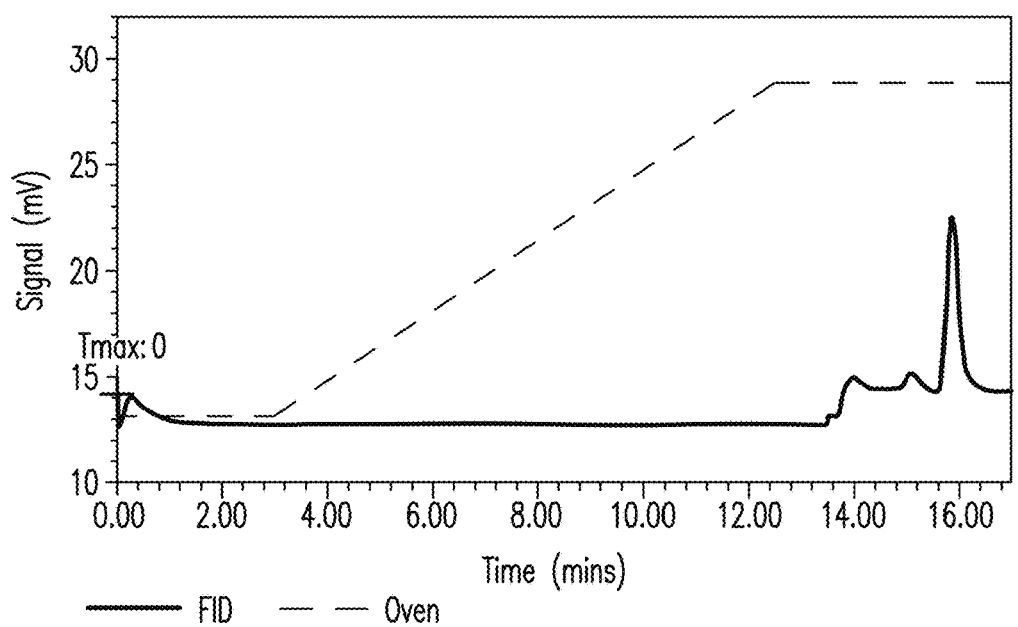
FIG. 25 is a pyrogram obtained by programmed pyrolysis on a thermally immature sample.
Figure 26:
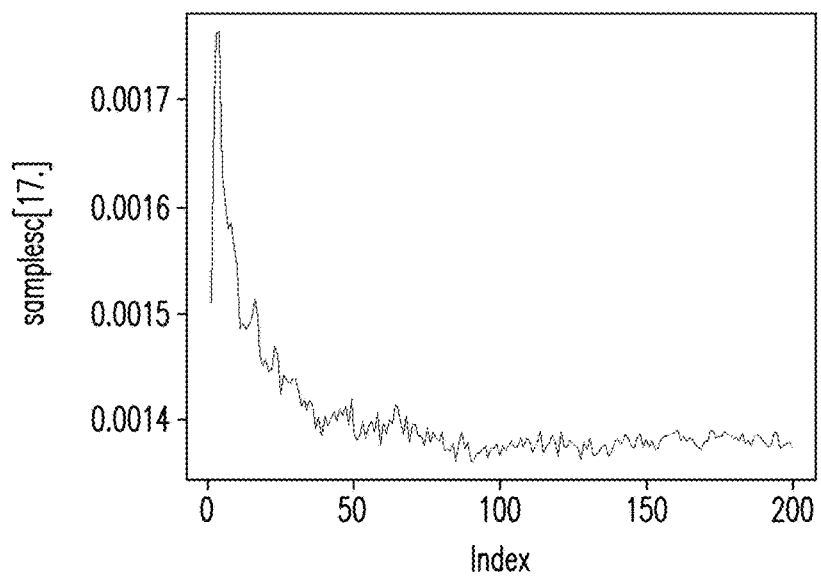
FIG. 26 shows a decay curve with intensity values with respect to the shot number as acquired from LIBS using a method according to an example of the present application for comparison to the results shown in FIG. 25. Whereas the pyrogram in FIG. 25 was unable to determine thermal maturity, the decay curve from LIBS showed behavior consistent with a thermally immature sample (FIGS. 27-28).
Figure 27:
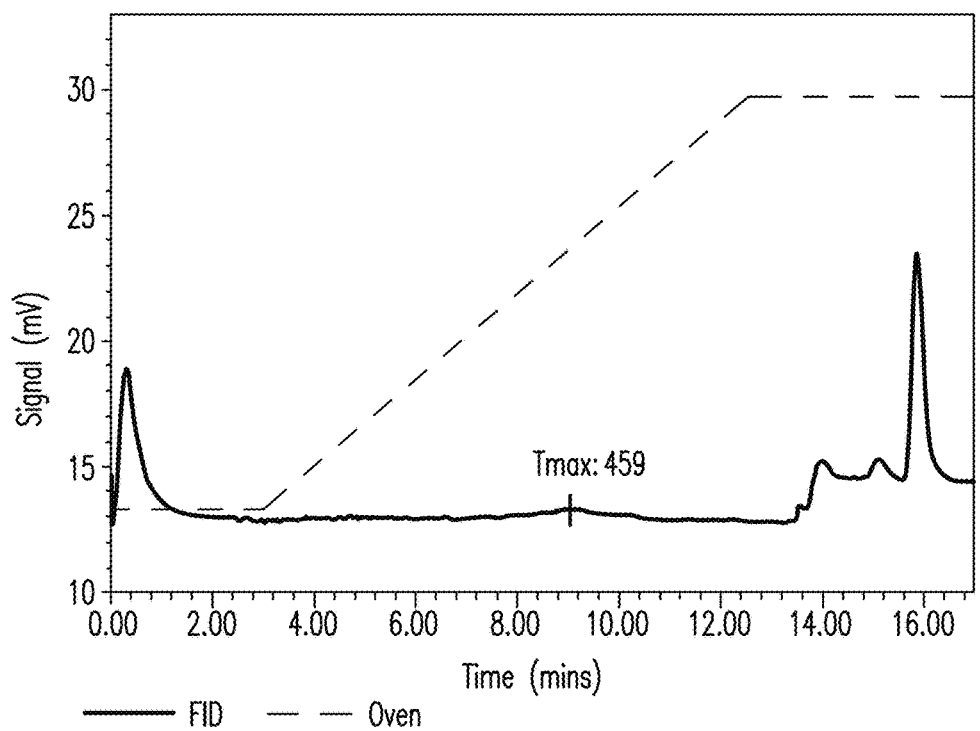
FIG. 27 is a pyrogram obtained by programmed pyrolysis on a thermally immature sample.
Figure 28:
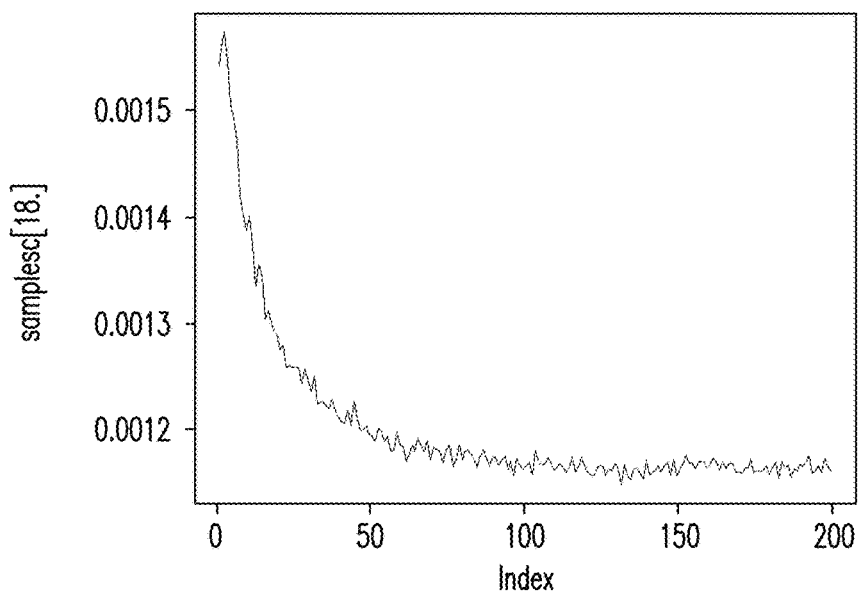
FIG. 28 shows a decay curve with intensity values with respect to the shot number as acquired from LIBS using a method according to an example of the present application for comparison to the results shown in FIG. 27.

Results for samples that had LIBS spectral acquisition measurements determined for them according to a method of the present invention that are shown in the some of the figures described herein, such as FIGS. 13-14, and focus on hydrogen, but carbon (FIG. 15), oxygen, or other elements associated with organic matter can be measured similarly. The curves are created by integration of the hydrogen peak. However, more advanced analysis on one or more other peaks, partial spectra or whole spectra for each, or a subset, of the laser shots may be used to give other information on thermal maturity, kerogen/bitumen discrimination and organic matter typing. Samples not containing significant quantities of organic matter usually show a stable behaviour of the hydrogen peak (FIG. 13F). Certain settings of the laser size, power, duration and repetition rate can be optimal for characterizing some samples while other types of samples will have different setting requirements for optimal characterisation. Thermally mature samples show longer decay curves. Conversely, observing the increase of the elements associated with inorganic material in organic rich samples may also yield information on sample properties. Unlike typical LIBS measurements, which are considered non-destructive, considerable sample alteration may occur near the point of laser ablation.

In accordance with the practice of examples of the present invention, a LIBS analyzer that has the configuration shown in FIG. 2 was used. The LIBS analyzer used was commercially obtained from TSI Incorporated. The measurements were performed on the company's (TSI) penultimate model of LIBS analyzer and has the name Insight. Measurements were made using a 50 mJ laser operating at 60% power. Shot rate was nominally 10 Hz, though actual rate appeared to be close to 5 Hz, and laser duration was 200 microseconds (μs). Laser spot size on the sample was 200 micrometers (μm). Samples were placed on a three axis adjustable stage. A high-resolution camera was used to adjust the sample stage to the correct distance for measurement and see where on the sample the laser would be fired. Argon was flowed over the sample during measurement to avoid unwanted influence of elements commonly present in air (H, N, O, etc.) in the measurement. 200 shots of the laser, including acquisition of the light spectra after each laser shot, were measured. This appears to be adequate for some samples, though it appears more shots can be required for some of the very organic rich or very thermally mature samples to reach an equilibrium.

Optionally, one or more cleaning shots can be made on the sample before the LIBS spectra measurement. The sample may be subjected to cleaning shots as-is without the need for any additional previous or subsequent sample preparation before the sample is subjected to the measurement shots. As indicated, cleaning shots may be performed in order to remove surface imperfections or contaminants, but a weak power setting typically is used for the cleaning shots in order to avoid pyrolysation of the nearby organic matter. In the measurement shots, the LIBS spot focus can be solely on organic matter of the sample, or the spot can focus on both organic and inorganic matter and the contribution of the organic matter is deconvoluted through manual or uni or multivariate analysis or cluster analysis or self-organising maps or neural nets or metaheuristic procedures (e.g. particle swarm optimization, genetic algorithms, etc.). A single LIBS measurement or multiple LIBS spectral measurements can be used for the geochemical analysis.

In LIBS, the light emitted from the plasma as it cools is measured. The measured light is usually in the wavelength range of 180 to 900 nm. Certain elements will have peaks located at distinctive wavelengths (FIG. 3). Sometimes there exists multiple peaks for a given element, though frequently one peak of an element is more desirable for analysis (e.g. stronger intensity, fewer nearby peaks that could interfere) than other peaks produced by that element (FIG. 3, e.g., Al, Be).

Figure 4:
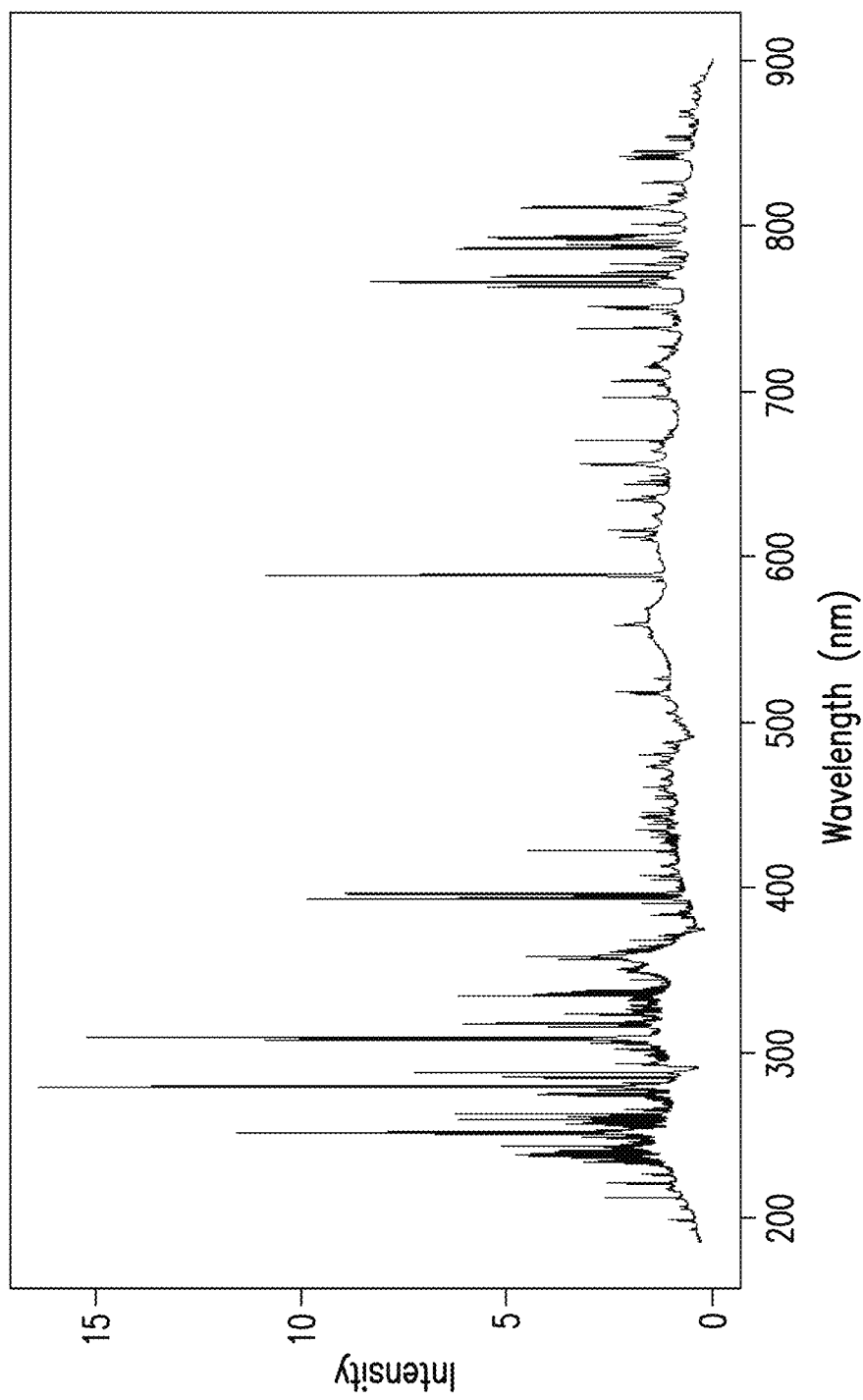
FIG. 4 shows emission peaks for elements at respective wavelengths from a sample according to an example of the present application.
Figure 5:
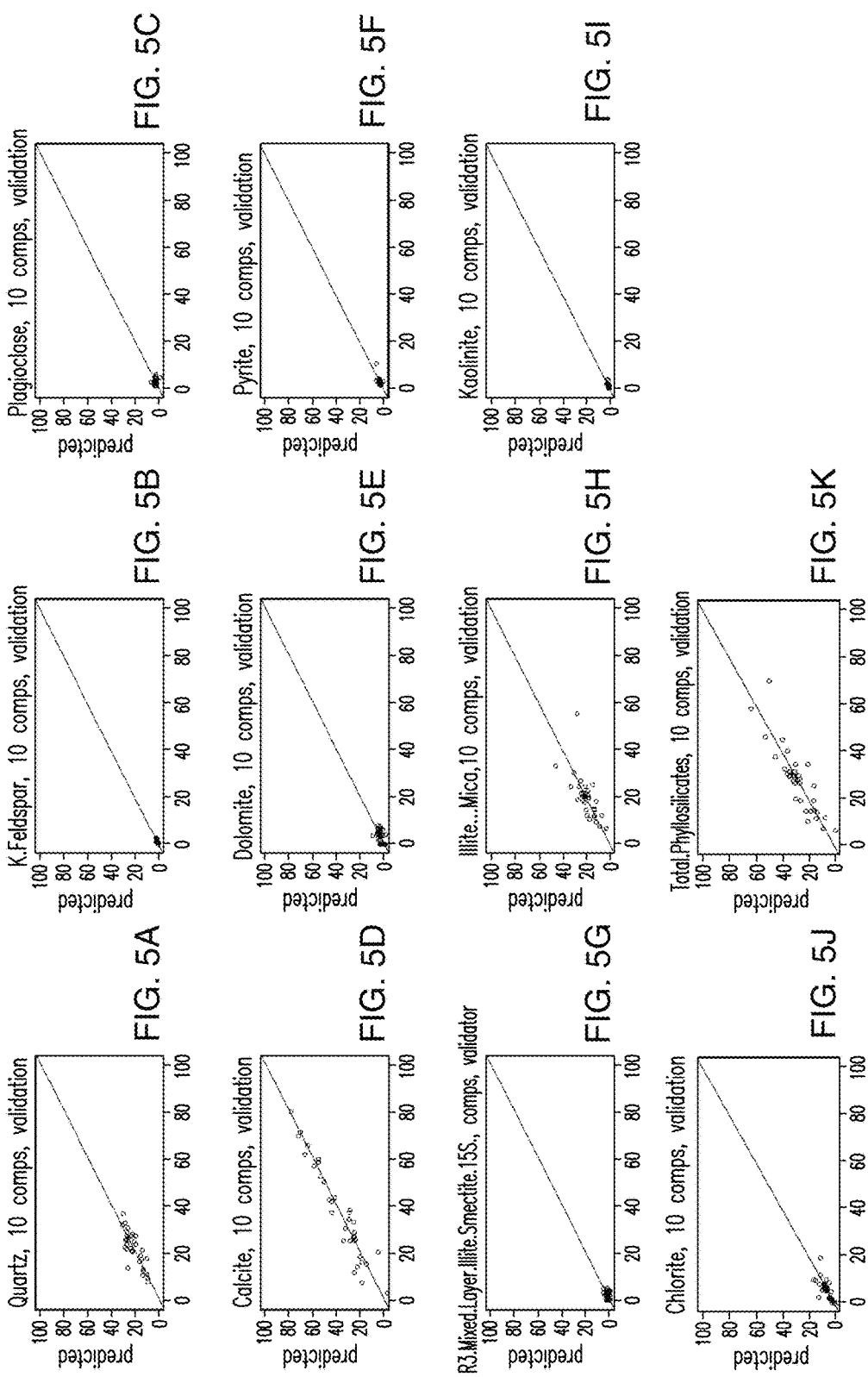
FIGS. 5(A)-(K) shows mineralogy predicted by LIBS for the indicated materials using Partial Least Squares Regression using the LIBS spectra obtained after shots where the normalized peak area of elements had stopped changing and stabilized into a plateau.

The method of pre-processing the data can involve integrating the intensity for a given peak. Because there may be intensity changes in the spectra depending on the exact volume of sample ablated, the whole spectrum was normalized at the start of pre-processing. This was performed by dividing the entire spectrum by the total signal intensity (the summation) of the spectrum. There are other possible ways of normalizing (e.g. normalizing to a strong peak), but this appeared to be the best way to normalize. This was then repeated on the spectrum from the next laser shot on a given sample until all the spectra from all the laser shots had been normalized (FIG. 4).

Figure 8:
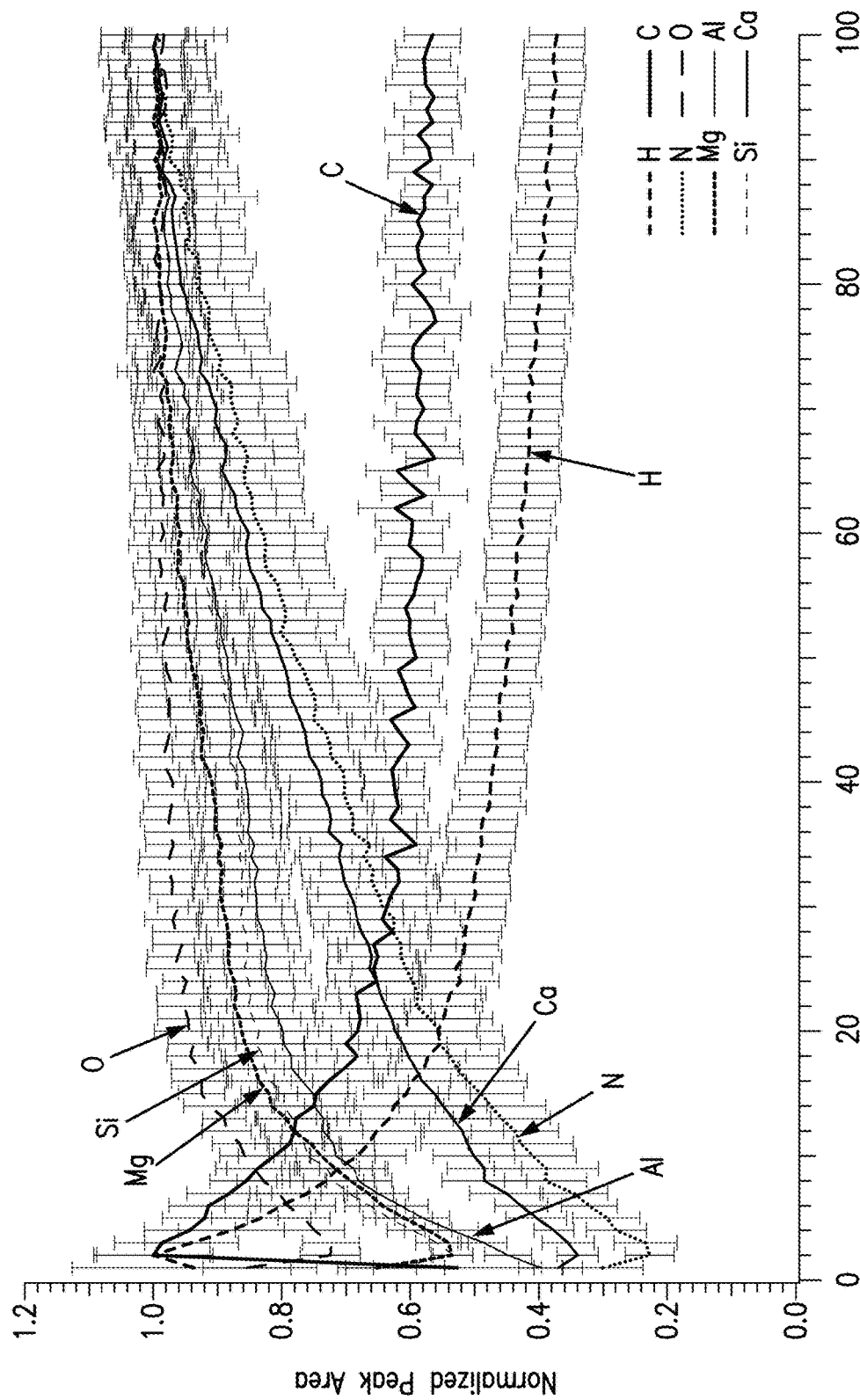
FIG. 8 shows normalized peak area values with respect to the shot number for a number of different indicated elements as acquired from LIBS using a method according to an example of the present application.

After the spectra were all normalized, the intensity of each of a desired peak relating to a particular element was integrated (FIG. 8). Because the peaks have finite width, in order to capture the complete intensity, three points on either side of the center of the peak were also included in the integration and the value recorded. This is repeated for the next shot number until the intensity for the peak for each shot of the laser has been determined. The integrated intensity of the peak is then combined into a vector, which may be plotted visually to aid in understanding the changes in the element with shot number. This vector then shows how the intensity, and thus the concentration, of the element changed with each firing of the laser. This may be repeated for other peaks, either different peaks of the same element, or peaks relating to other elements to produce vectors relating to how each of those elements decay. Because some elements produce stronger peaks than others, direct comparison of intensities versus one another does not appear possible, though some conversion factors may exist that may make that possible. The peaks used for the analysis in this example were the H peak located at 656 nm, the C peak at 247 nm and the O peak at 777 nm. For the organic elements, a decay of signal for organic rich samples can be frequently seen. This is because the laser serves to pyrolyse some of the material surrounding the location of the laser spot, such that there is then less organics in the nearby material, which is observed on the next shot of the laser. However, the exact behavior may change depending on surface contamination and the composition of the inorganic matrix.

More advanced methods may be applied for pre-processing the spectra instead of integrating the intensity of a peak and plotting its change as a function of shot number, such as using the actual peak and its distribution of intensity for analysis instead of simply integrating its intensity, or using multiple peaks for an element, or combining the peak or peaks of one or more elements, or potentially using a sub-spectra or simply the whole spectrum for analysis.

The entire LIBS spectra can be used for the geochemistry analysis. One or more individual peaks in the LIBS spectra can be used for the geochemistry analysis. One or more sub-sections of the LIBS spectra can be used for the geochemistry analysis. The intensity decay of peaks can be used for analysis of geochemistry properties. The intensity increase of peaks can be used for analysis of geochemistry properties. The raw data can be used for the analysis. The data can be pre-treated before analysis, such as applying an exponential fitting, bi-exponential fitting, multiple-exponential fitting, inverse Laplace transform, Gaussian decay fitting, or other analysis or filter. Combinations of these may be used.

Figure 6:
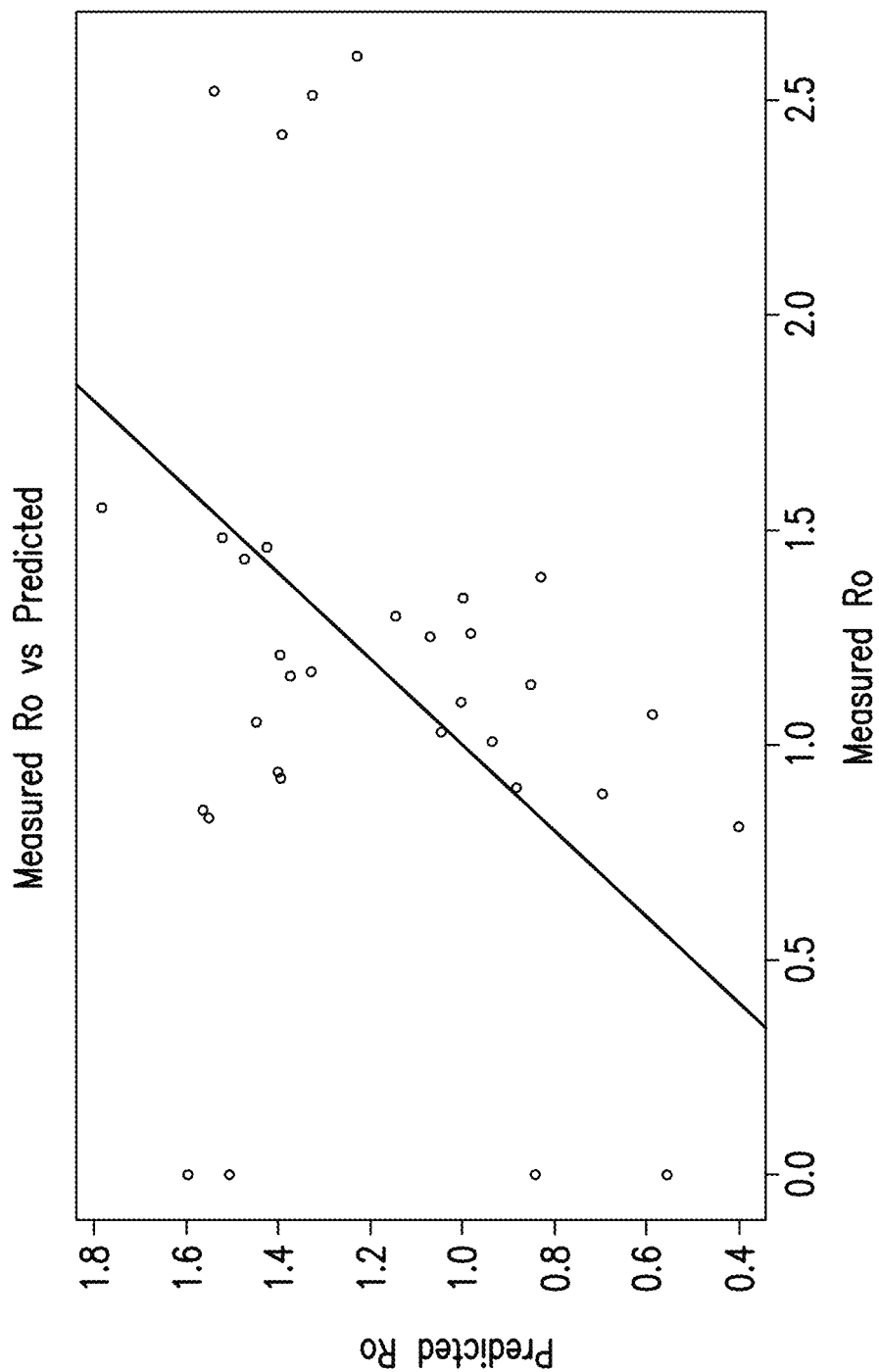
FIG. 6 shows correlation of measured Ro versus predicted Ro from LIBS using Partial Least Squares Regression using the LIBS spectra obtained after shots where the normalized peak area of elements had stopped changing and stabilized into a plateau.
Figure 7:
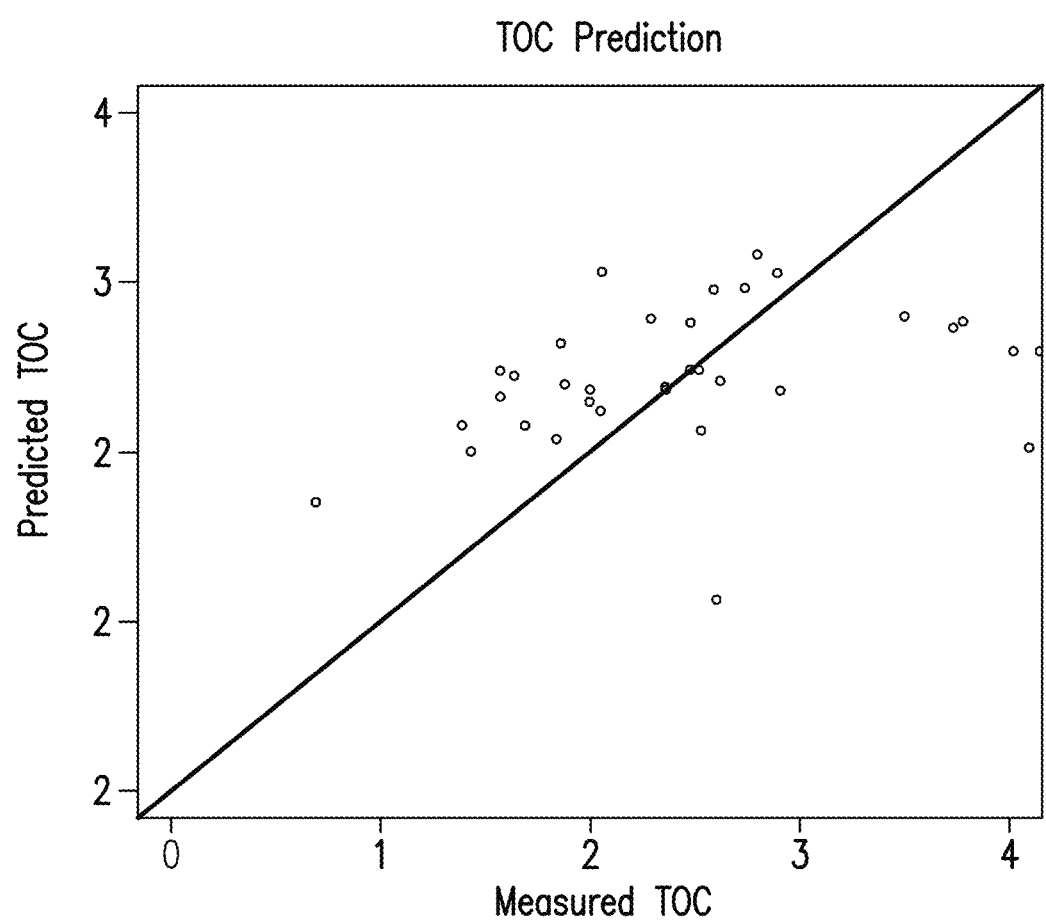
FIG. 7 shows correlation of measured TOC versus predicted TOC from LIBS using Partial Least Squares Regression using the LIBS spectra obtained after shots where the normalized peak area of elements had stopped changing and stabilized into a plateau.

As the approach used here, the individual intensity vectors for H, C and O (each of length 200) are combined together into one long vector (length 600) for each sample. The long vector of each sample is then combined into a matrix of all the samples (30 by 600). Once the pre-processed spectra have been created, analysis can be performed on the data. A partial least square analysis is then used to correlate the decays to geochemical properties. The partial least squares works by trying to correlate the highest variance in the data with the highest variance in the property to be predicted, in our case things like thermal maturity or bitumen content. Some of the data were rather noisy, so a moving average was applied to the data before analysis to smooth out the effects of noise. A very good predictive value is seen for many geochemical parameters such as TOC, S1, S2, Ro and S3 (FIGS. 16-20). In contrast, geochemistry prediction appears to be very poor (FIGS. 6-7) using standard LIBS methods, which will use cleaning shots until the peaks in LIBS spectra have stabilized and then analyse the spectra from subsequent laser shots.

TOC, S1, S2, and S3 have been described hereinabove. With regard to the parameter Ro, vitrinite is found in many kerogens, and reflectivity can be measured by a microscope equipped with an oil-immersion objective lens and photometer. Vitrinite reflectance measures can represent the percentage of light reflected in oil, designated as Ro. Ro values can be indicators of thermal maturity, and can vary with the type of organic matter. For example, going from high Ro values to lower Ro values, the higher values may relate to dry gas and progressively lower values can relate to gas with a tendency toward oil generation, then wet gas, then predominantly oil, and lastly immature kerogen at the lowest values.

Other methods may be used to analyse the LIBS data such as simple univariate analysis, multivariate analysis including but not limited to: principle component analysis, principle component regression, multiple linear regression, non-negative linear regression, cluster analysis, neural nets, self-organising maps, metaheuristic procedures (e.g. particle swarm optimization, genetic algorithms, etc.) and CAR (clustering assisted regression) analysis. Manual evaluation (i.e., looking at the spectra and making a judgment call) also may be used.

Figures 29, 30, 31:
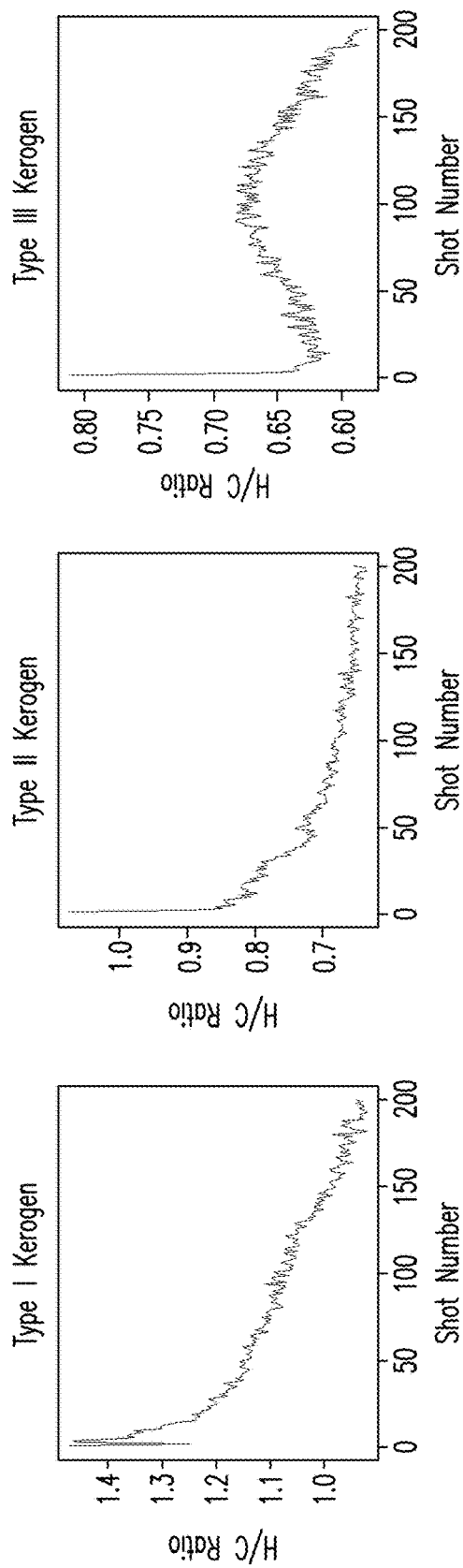
FIG. 29 shows H/C atomic ratio values with respect to shot number for Type I kerogen according to an example of the present application.
FIG. 30 shows H/C atomic ratio values with respect to shot number for Type II kerogen according to an example of the present application.
FIG. 31 shows H/C atomic ratio values with respect to shot number for Type III kerogen according to an example of the present application.
Figure 32:
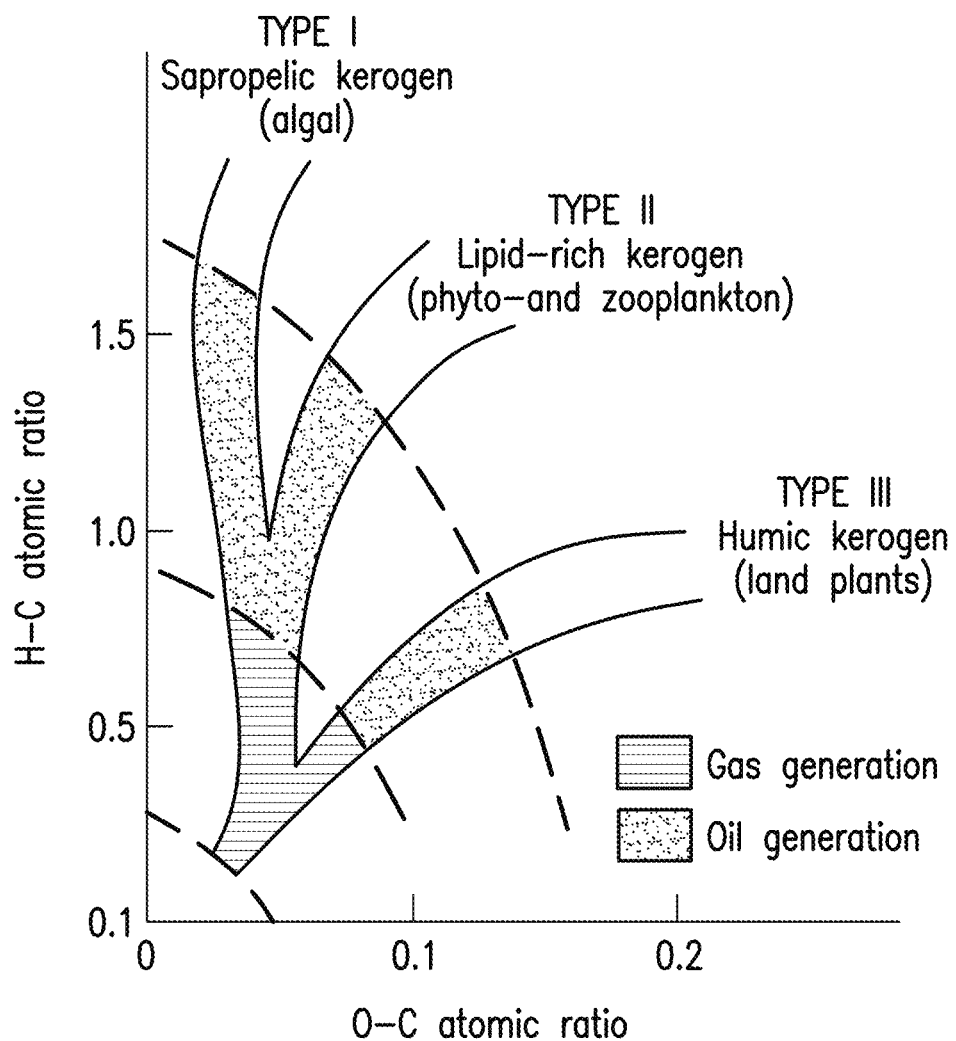
FIG. 32 shows H/C atomic ratio values with respect to O—C atomic ratio and correspondence to Type I, II, or III kerogen and gas or oil generation.

In addition, ratios between elements can be created by dividing the intensity vector for one element by another, for example H/C by dividing the H intensity vector by the C intensity vector (FIGS. 29-31). These change with shot number as well, though the intensity appears to be different depending on kerogen type. Using this procedure, the H/C and H/O ratios can be obtained. The H/C and H/O ratios are used to provide information on kerogen type (similar to a Van Krevelen diagram) and possibly information regarding thermal maturity (FIG. 32) or organic matter type.

The inventive method can use these ratios of lighter elements, e.g., ratios using amounts of elements having an atomic weight of about 12 or lower that can be acquired with the LIBS-based method of the present invention, to great benefit.

Univariate analysis or multivariate analysis can be used to correlate the LIBS spectral data to determined values for H/C ratio, H/O ratio, hydrogen index, programmed pyrolysis, a thermal maturity property (e.g., thermal maturity, kinetic analysis), kerogen and bitumen content/discrimination, kerogen type, hydrocarbon content, hydrocarbon type, or any combinations thereof. Though H/C ratio and H/O ratio are used in these examples, the indicated univariate or multivariate analysis used in the method of the present invention also can be applied to other elemental ratios, and the indicated univariate or multivariate analysis can be applied to trace elemental content of the organic matter (e.g., sulfur (S), nitrogen (N), or other elements), oxygen index, or any combinations thereof.

The present invention further relates to a method for determining geochemical information relating to kinetic analysis of a sample, comprising: a) heating at least one sample by laser-induced pyrolysis, such as LIBS; b) monitoring the reaction rate, such as a value of the Arrhenius equation rate constant k, of at least one sample comprising at least one of: i) monitoring changes in amounts of elements associated with organic matter and hydrocarbons for a portion of at least one sample that is heated by the laser-induced pyrolysis, ii) collecting and analysing hydrocarbon species produced by pyrolysis of a portion of at least one sample from the laser-induced pyrolysis by a flame ion detector or gas chromatography-mass spectrometry (GC-MS), iii) monitoring the weight of at least one sample during the laser-induced pyrolysis of at least one sample, iv) monitoring the temperature of at least one sample and determining the amount of energy inputted into the portion of the sample by the laser during the laser-induced pyrolysis. The LIBS spectral data further can be used to perform a rapid kinetic analysis for determining how thermal maturation of one or more samples progresses depending on the energy input. For purposes herein, a reaction rate can refer to a generation rate for hydrocarbons from thermally-induced decomposition of kerogen in the sample, e.g., a hydrocarbon generation rate. In evaluating generation rates using kinetics analysis, the quantity, types, and rate at which hydrocarbons are generated from kerogen given particular heating conditions can be estimated in addition to determining what type and quantity of hydrocarbons the kerogen may already have produced. Kinetic analysis can be used to help understand the conversion process of organic matter from kerogen into products like thermobitumen, oil, gas and pyrobitumen. This can be used to help understand what petroleum products may have been produced by source rocks and reservoir rocks, such as for the case of tight oil and gas shales, and for the case of oil shale, what petroleum products may be produced in the future, and at what generation rates. Kerogen maturation can be considered to be tied to chemical reaction rates. Many kinetic formulations assume that kerogen directly converts to oil and gas hydrocarbons, or other formulations assume that kerogen converts to hydrocarbons via bitumen intermediate. Kinetic models can use the Arrhenius equation, which is given by equation (1): $k=Ae^{-E_a/RT}$. In the indicated Arrhenius equation, k is the rate constant of the chemical reaction, such as the reaction rate constant for loss of the reacting (decomposing) species of kerogen in the transformation of kerogen to hydrocarbons, which can be expressed as the change in the molar mass of the reactant with respect to time. A is the pre-exponential or frequency factor, which describes the number of potential elementary reactions per unit time (e.g., in units of $min^{-1}$) $E_a$ is the activation energy that describes the energy barrier that must be exceeded in order for a reaction to occur (in energy/mole, e.g., kiloJoule/mole). R is the gas constant (e.g., 0.008314 kJ/° K-mole), and T is the absolute temperature (° K). If kinetic analysis is performed by running programmed pyrolysis measurements, the temperature of the oven is known, the quantity of produced organic products monitored and can be used to obtain the distribution of $E_a$ value for a sample. When determining $E_a$ from data obtained using a pyrolysis oven in programmed pyrolysis measurements, a challenge is in determining the value of A. Typically several programmed pyrolysis measurements can be performed with different heating rates for purposes of solving for the value of A. In kinetic analysis that uses a multiple-heating ramp open-system pyrolysis strategy, kinetic analyses begins with pyrolysis of source rock samples in an oven using two, three, or more different heating rates (e.g., different ° C./min heating rates). When the reaction in question is first order and occurs under isothermal conditions, then activation energies ($E_a$) and frequency factors (A) may be obtained from a plot of the natural logarithm of the reaction rate (ln k) versus the inverse of the absolute temperature (1/T), where k is the reaction rate (mass/time) and T is the temperature (T in ° K). Activation energies and frequency factors also may be found using non-isothermal experiments as long as the temperature varies at a constant rate. An approximate solution for the Arrhenius equation under those conditions can use the Kissinger method or other approaches. E.g., S. H. Nordeng, "Evaluating Source Rock Maturity Using Multi-Sample Kinetic Parameters . . . ," Geol. Investig. No. 164, North Dak. Geol. Survey, 2013, pp. 1-19. In some cases, A is either fixed or assigned from a priori knowledge such that only one heating rate is necessary in a one-run, open-system pyrolysis experiment ("single ramp" pyrolysis). The present invention can include a method for determining kinetic properties such as reaction rates or activation energies for a sample that does not require heating of an entire sample in a pyrolysis oven and can provide reliable information on how a sample has and will thermally mature.

Instead of heating an entire sample in an oven to generate data for kinetic modeling, in the present invention a laser, such as applied using LIBS, can be used to pyrolyse the sample at a single or multiple selected locations, such as discrete spots on the sample. Then at least one location of the sample can be subjected to a plurality of successive measurement shots of laser light with each measurement shot at least partly vaporising and turning a portion of the sample at the location subjected to the successive shots of laser light into plasma to cause spectral emission, which is detected after each measurement shot with at least one spectral detector. The spectral data acquired from the spectrum detector can be preprocessed, such as by the indicated univariate analysis or multivariate analysis. The acquired spectral data, raw or preprocessed, can be used in a kinetic analysis of the sample. A laser, such as applied using LIBS, can be used as the source of heat that pyrolyzes the sample, and k, $E_a$ and/or other kinetic property data can be determined for the laser-heated portion of the sample by one or several different strategies from the spectral data acquired from using LIBS as indicated. In this respect, k, $E_a$ and/or other kinetic property data can be determined from the indicated spectral data obtained during laser heating of a portion of the sample based on changes in amounts of elements associated with organic matter and hydrocarbons, e.g., by monitoring the increase or decrease in elements associated with organic matter and hydrocarbons. In another respect, k, $E_a$ and/or other kinetic property data can be determined from spectral data obtained during the laser heating of a portion of the sample by collection and analysis of the produced hydrocarbon species from LIBS further by a flame ion detector or gas chromatography-mass spectrometry (GC-MS) or by monitoring weight of the sample during LIBS. Alternatively, as the amount of energy inputted into the system by the laser is known, by monitoring the temperature of the sample, k can be calculated for a portion of the sample that is heated by LIBS. Combinations of these strategies may be used. In these respects, a single or multiple LIBS measurements can be performed which can have the same or different settings of the laser power, repetition rate or spot size. As indicated, a LIBS measurement can comprise successive shots of laser light with each measurement shot at least partly vaporising and turning a portion of the sample into plasma to cause spectral emission, which is detected after each measurement shot. Temperature can be assumed based on prior information, or calculated through the intensity and or width of the LIBS peaks in the spectra, or by monitoring the sample through a device such as an infrared (IR) camera. A combination of monitoring the inputted energy to the system, the sample temperature, and produced products can provide an understanding of the chemical kinetics of the organic matter maturation, such as the reaction rate or distribution of activation energies. If an IR camera is used in determining the sample temperature resulting from the laser treatment, in addition to understanding the kinetics analysis of the organic matter, the heat transfer properties of the shale can be observed by monitoring the temperature of the sample after laser shots and how the temperature changes around the laser spot as a function of time. The generated kinetic property data by the inventive method can be locationally-mapped across a surface of the sample, and/or for different depths of the same sample (or different sample).

Figure 9:
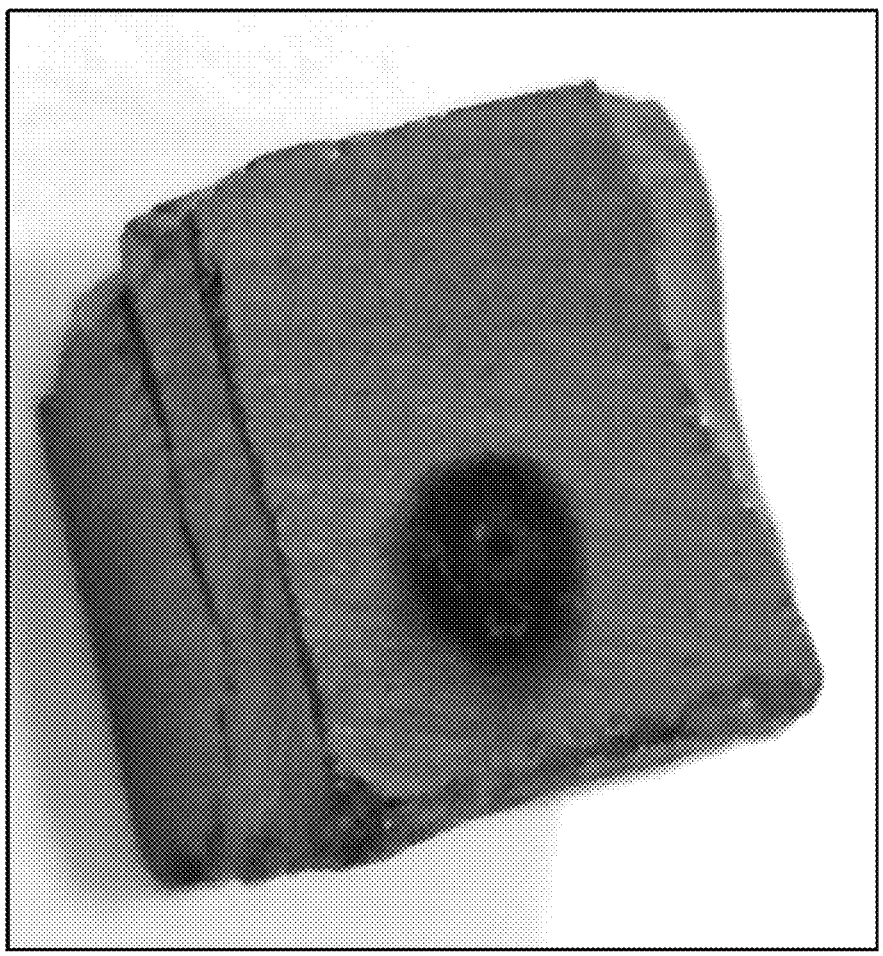
FIG. 9 is an enlarged photograph of an organic rich rock sample that includes a laser spot with pyrolysed surrounding matrix formed in a rock sample using LIBS performed in a manner according to an example of the present application.
Figure 10:
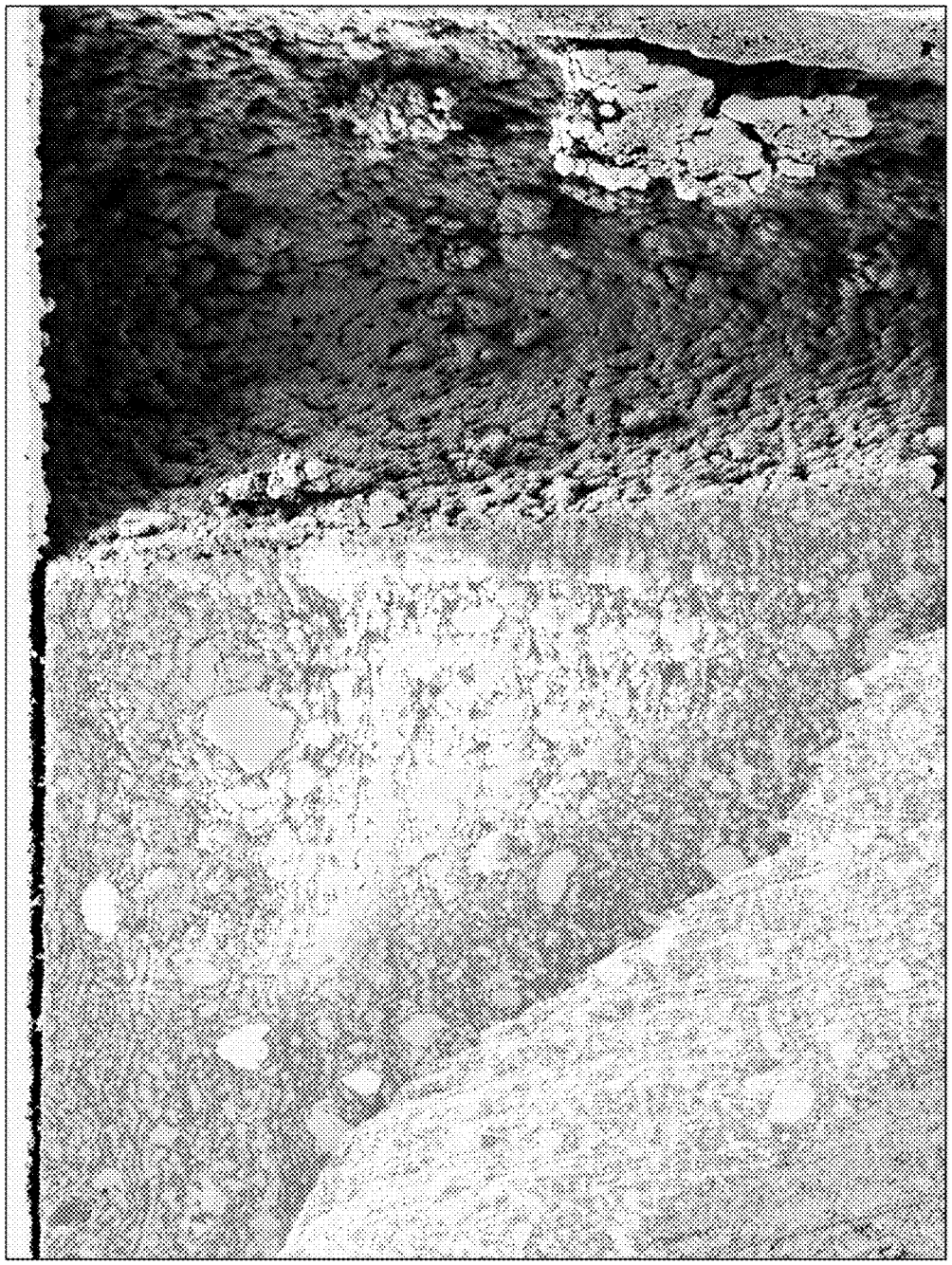
FIG. 10 is an SEM of a rock sample which is analysed in a method according to an example of the present application.
Figure 11:
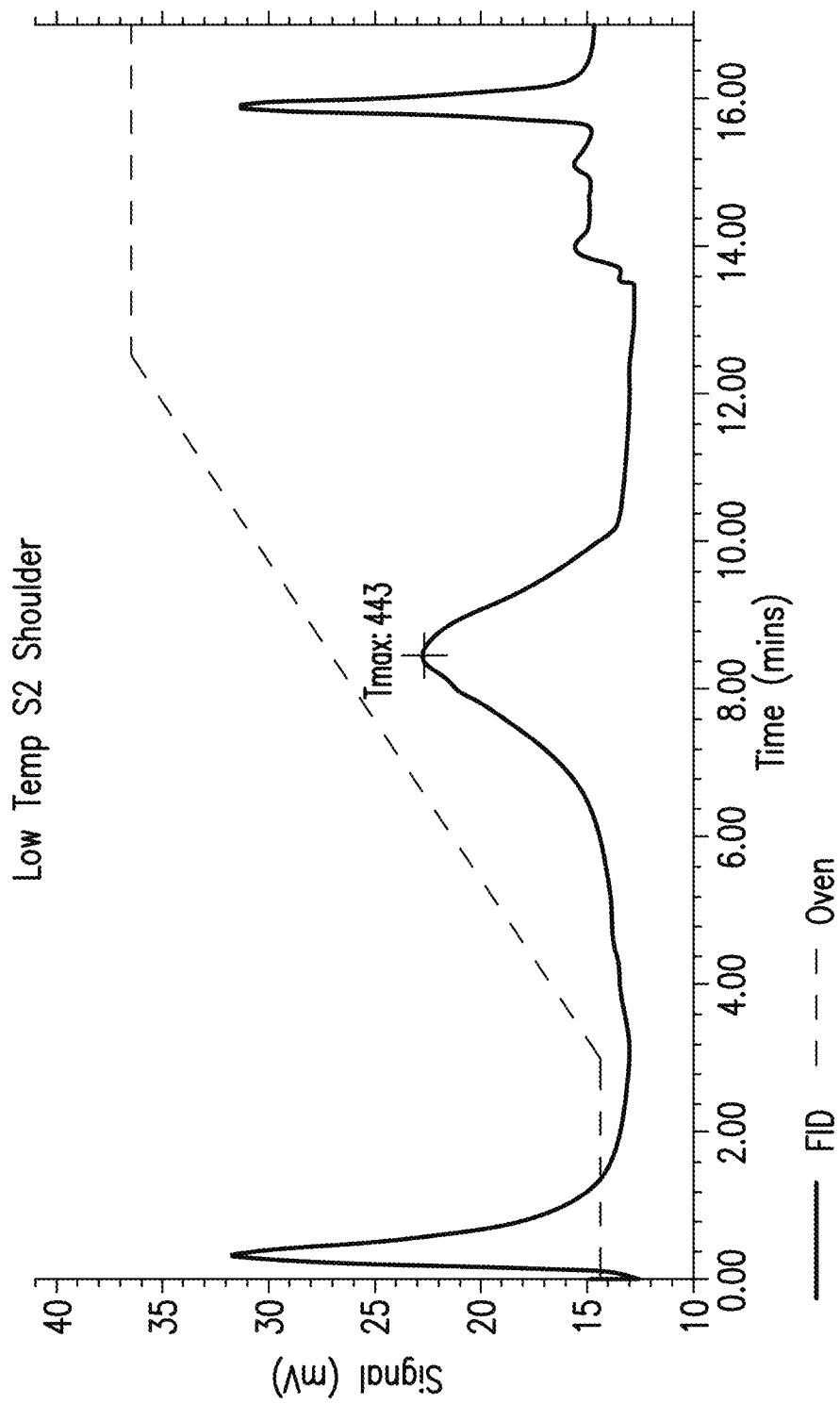
FIG. 11 is a pyrogram obtained by programmed pyrolysis on a sample.
Figure 12:
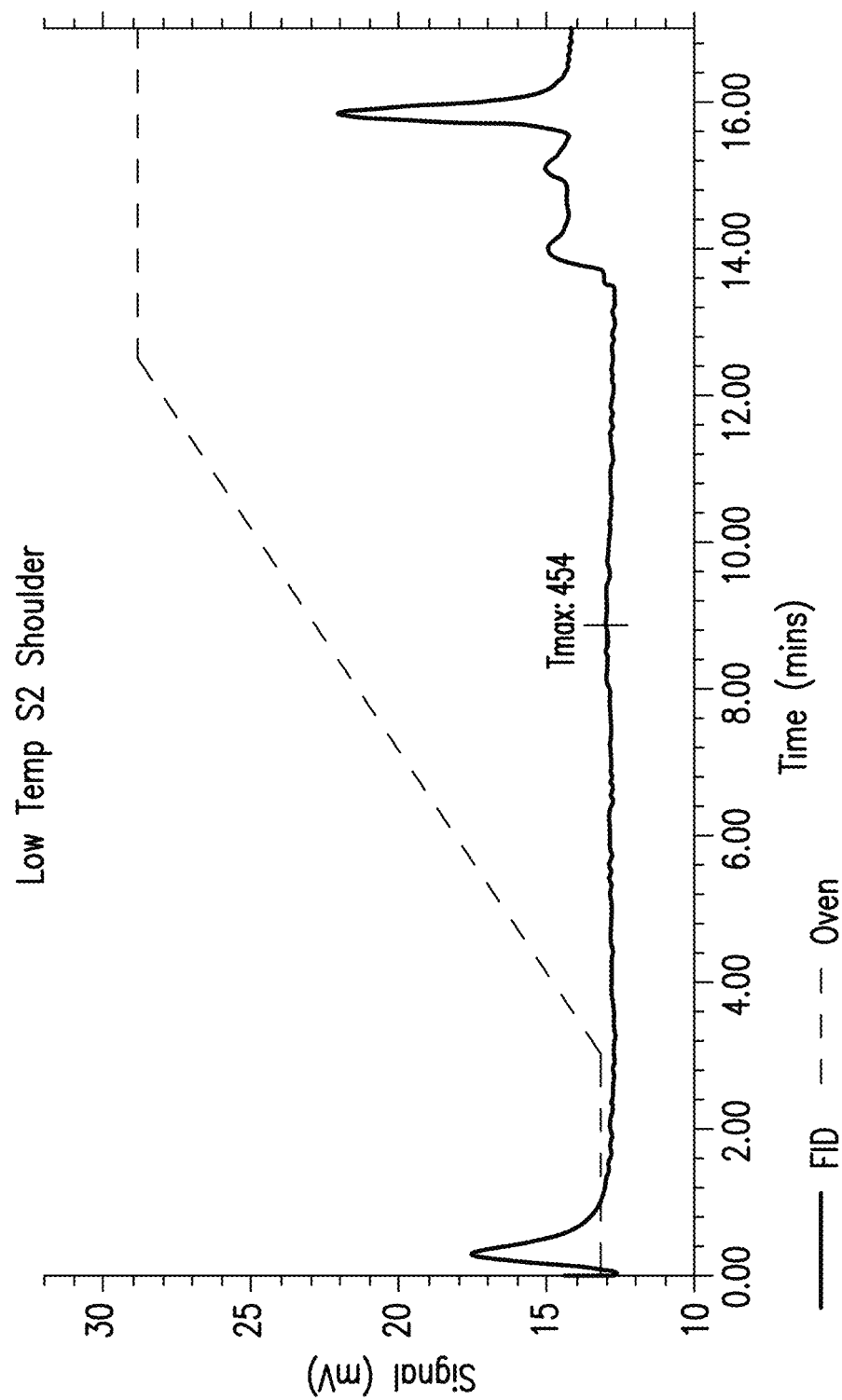
FIG. 12 is a pyrogram obtained by programmed pyrolysis on a sample.

The digital photographic image shown in FIG. 9 shows a dark ring around the laser spot where the organic matter in the surrounding matrix of the laser-impinged sample has been pyrolysed. Charring seems to be worst in samples of higher thermal maturity.

Though not limited thereto, a LIBS system which may be adapted for implementing a method of the present invention can have a laser capable of causing vaporisation and turning into plasma a part of the geological sample and a spectral detector with a wide spectral range and a high sensitivity, fast response rate, time gated detector. These components can be coupled to a computer which can rapidly process and interpret the acquired data.

Suitable lasers can include solid state lasers such as the 1064 nm Nd:YAG laser, harmonic wavelengths of the Nd:YAG laser, e.g., 532 nm, 355 nm, and 266 nm; gas lasers such as excimer lasers, e.g., 308 nm XeCl, or 248 nm KrF excimer lasers; carbon dioxide lasers; liquid lasers such as dye lasers; or any wavelength/frequency shifting, harmonic generation or combinations of the above. Lasers other than those specifically mentioned may also be used.

Each of the plurality of detectors can comprise a spectrometer adjusted to a part of the spectral region. Each of the spectrometers, for example, may have a CCD detector associated with the spectrometer. The CCD detector may pass information on the spectral region to a data acquisition card or a data file in a computer or memory space. This data may then be analysed to determine the presence of one or more elements in the material and to determine the amount or concentration of the element in the geological material in manners described herein.

Spectrometer types suitable for use in the present invention can include grating and prism spectrographs; interferometers, such as etalon and scanning interferometer types; and filters, including coloured glass or interference filter types which allow transmission or reflection of a portion of the spectrum. Each of the plurality of spectral detectors can comprise a spectrometer adjusted to detect a contiguous part of the spectral region. Detectors which can be used in the present invention include the above-indicated CCD's (charged-coupled detectors) or other detectors such photo-diode arrays, vidicons, photomultiplier tubes and photodiodes. A multi-channel broadband spectrometer ($\lambda$ range of 190-950), Echelle spectrometer with iCCD detector may be used ($\lambda$ range of 200-900), or other spectral detectors may be used. A person skilled in the art can readily appreciate which detector(s) can be used.

The system or apparatus of the present invention can further comprise a controller for controlling the firing of the laser and for controlling and synchronising operation of the plurality of detectors therewith. That is, the controller may include a timing circuit to fire the laser at specified times and to operate the detectors at other specified times. The controller, for example, can simultaneously turn on a plurality of spectrometers at a short time after the laser is fired, and the plural spectrometers being otherwise turned off. In place of the timing circuit, the controller may comprise control software to control operation of the laser and the detection means. The controller can operate under the direction of control software to send a control signal which causes the laser to emit a pulse of laser light and to send a control signal to each of the plurality of spectral detectors which turns on the spectral detectors. In such manners, the controller can be used to synchronise operation of each of the plurality of detectors such that the plurality of detectors simultaneously detect spectral emissions from the material.

The systems or apparatus can also include one or more optical systems to focus the laser light on the geological material and to focus the spectral emissions on the plurality of detectors. The one or more optical systems may include one or more lenses, optical fibre, prisms, beam splitters or other optical components. Although suitable optical systems are typically needed, the specific design of the optical system does not form part of the invention and a person skilled in the art should be able to design a variety of different suitable optical systems.

The indicated system or apparatus of the present invention may be suitable for analysing material in a laboratory in a building, or in-the-field, such as in a mobile transport vehicle or mechanism on the ground or underground.

As indicated, the geochemistry parameters which can be obtained by a method of the present invention can be used as input into a process for determining spatially resolved geochemistry of a geological material and/or as integrated with other kinds of geochemical parameter data, for use in characterising or modeling of the sample and/or geological reservoir form which the sample was obtained. For example, the spectral data can be integrated into two or three dimensional models created from spatial imaging, to generate spatially resolved geochemical information on the sample. Appropriate spatial geochemistry information in the 2D or 3D models can be determined through image segmentation, assigned manually, determined by capillary pressure simulation or measurements, or determined from previously spatially resolved spectral measurements. Modes of spatial information acquisition on geological samples are known in the industry, including, e.g., X-ray CT, NMR, SEM, FIB-SEM, neutron scattering, thin sections, and high resolution photography. These can be adapted for use in a process of obtaining spatially resolved geochemical information with integration of the spatial information with geochemistry parameter information obtained using the method of the present invention.

The present invention includes the following aspects/embodiments/features in any order and/or in any combination:

1. A method for analysing a geological sample, comprising:
   subjecting at least one location of a geological sample to a plurality of successive measurement shots of laser light with each measurement shot at least partly vaporising and turning a portion of said sample into plasma to cause spectral emission;
   detecting said spectral emission after each said measurement shot with at least one spectrum detector;
   pre-processing collected data from the spectrum detector as needed to alter the data into a form that is suitable for analysis; and
   analyzing the data, raw or pre-processed, to determine at least one geochemistry parameter.

2. The method of any preceding or following embodiment/feature/aspect, further comprising subjecting the at least one location of a geological sample to at least one cleaning shot of laser light before the subjecting of the at least one location of a geological sample to the plurality of successive measurement shots.

3. The method of any preceding or following embodiment/feature/aspect, wherein the pre-processing comprises integration of one or more peak areas to produce an intensity curve or curves, selection of the maxima of a peak for successive shots to produce an intensity curve, the actual peak spectra for successive measurement shots, or sub-regions of the spectra or the whole spectra for the successive measurement shots. Pre-processing may include two or more of the mentioned steps.

4. The method of any preceding or following embodiment/feature/aspect, wherein the preprocessing comprises normalization, filtering, application of a function (e.g. taking a derivative), pre-treatment by applying an exponential fitting, bi-exponential fitting, multiple-exponential fitting, an inverse Laplace transform, a Gaussian decay fitting, compiling the data from the successive laser shots into a matrix, single vector, or other combined form. Pre-processing may include two or more of the mentioned steps.

5. The method of any preceding or following embodiment/feature/aspect, wherein the geochemistry parameter is obtained wherein manual or uni or multivariate analysis or cluster analysis or self-organizing maps or neural nets or metaheuristic procedures (e.g. particle swarm optimization, genetic algorithms, etc.) is used to correlate the collected data, raw or pre-processed, to determine values for at least one elemental ratio, trace elemental content of the organic matter, hydrogen index, oxygen index, programmed pyrolysis, thermal maturity property (e.g., thermal maturity, kinetic analysis), kerogen and bitumen content/discrimination, kerogen type, hydrocarbon content, hydrocarbon type, or any combinations thereof.

6. The method of any preceding or following embodiment/feature/aspect, wherein analyzing the data, raw or pre-processed, to determine at least one geochemistry parameter is obtained wherein manual or uni or multivariate analysis or cluster analysis or self-organising maps or neural nets or metaheuristic procedures (e.g. particle swarm optimization, genetic algorithms, etc.) is used to correlate the collected data, raw or pre-processed, to determine values for H/C ratio, H/O ratio, trace elemental content of the organic matter for at least one of S and N or other minor element in the organic matter, hydrogen index, oxygen index, programmed pyrolysis, thermal maturity property (e.g., thermal maturity, kinetic analysis), kerogen and bitumen content/discrimination, kerogen type, hydrocarbon content, hydrocarbon type, or any combinations thereof.

7. The method of any preceding or following embodiment/feature/aspect, wherein said further subjecting comprises controlling operation of the laser and a plurality of said spectrum detectors to simultaneously detect spectral emissions from the geological sample across a plurality of different spectral regions.

8. The method of any preceding or following embodiment/feature/aspect, wherein the sample is a rock sample.

9. The method of any preceding or following embodiment/feature/aspect, wherein each of the spectrum detectors comprises a spectrometer having a CCD detector associated therewith.

10. The method of any preceding or following embodiment/feature/aspect, further comprising:
   (a) obtaining spatial information on the at least one sample; and
   (b) determining spatially resolved geochemical information for the at least one sample using the geochemistry parameter and the spatial information.

11. A system to perform the method of any preceding or following method.

12. The present invention further relates to a method for analysing a geological sample, comprising:
   subjecting at least one location of a geological sample to a plurality of successive measurement shots of laser light with each measurement shot at least partly vaporising and turning a portion of said sample into plasma to cause spectral emission;
   detecting said spectral emission after each said measurement shot with at least one spectral detector;
   optional or as needed preprocessing collected spectral data from the spectral detector to make it into a suitable form for analysis; and
   determining a reaction rate constant k for the Arrhenius equation of the at least one sample using the raw or pre-processed data from the spectrum detector.

13. The method of any preceding or following embodiment/feature/aspect, wherein the determining of the reaction rate constant k using the raw or pre-processed spectral data from the spectrum detector comprises at least one of:
   i) determining changes in amounts of elements associated with organic matter and hydrocarbons for a portion of at least one sample that is heated by LIBS,
   ii) analysing hydrocarbon species produced by pyrolysis of a portion of at least one sample from LIBS further by a flame ion detector or gas chromatography-mass spectrometry or by monitoring the weight of the sample during LIBS,
   iii) monitoring the temperature of at least one sample and determining the amount of energy inputted into the portion of the sample by the laser during LIBS, or using any combination of i), ii), and iii), such as ii) in conjunction with either i) or iii).

14. The method of any preceding or following embodiment/feature/aspect, wherein a prefactor in the Arrhenius equation is inputted based on a priori knowledge or solved for based on measurements performed on two or more different heating rates of the sample.

15. The method of any preceding or following embodiment/feature/aspect, wherein the different heating rates are obtained by one or more of different laser power, laser spot size or laser shot rate, or any combination thereof.

16. The method of any preceding or following embodiment/feature/aspect, wherein the kinetic analysis is used to either solve for the activation energy distribution in the sample or the reaction rates given a known input of energy.

The present invention can include any combination of these various features or embodiments above and/or below as set forth in sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for analysing a geological sample, comprising:
   subjecting at least one location of a geological sample to a plurality of successive measurement shots of laser light from a laser with each measurement shot at least partly vaporising and turning a portion of said geological sample into plasma to cause spectral emission;
   detecting said spectral emission after each said measurement shot with at least one spectrum detector;
   preprocessing of collected data from the at least one spectrum detector to form pre-processed data for analysis, wherein the preprocessing comprises one or more of:
   integration of one or more peak areas to produce an intensity curve or curves, or
   selection of the actual peak spectra for successive measurement shots, or
   selection of sub-regions of the spectra for the successive measurement shots, or
   selection of the whole spectra for the successive measurement shots; and determining bitumen content of the geological sample, kerogen content of the geological sample, or both using the pre-processed data from the at least one spectrum detector.

2. The method of claim 1, further comprising subjecting the at least one location of the geological sample to at least one cleaning shot of laser light before the subjecting of the at least one location of the geological sample to the plurality of successive measurement shots.

3. The method of claim 1, wherein the preprocessing further comprises one or more of filtering, application of a function, pre-treatment by applying an exponential fitting, bi-exponential fitting, multiple-exponential fitting, an inverse Laplace transform, or a Gaussian decay fitting.

4. The method of claim 3, wherein the preprocessing includes two or more of the integration of one or more peak areas to produce an intensity curve or curves, or selection of the actual peak spectra for successive measurement shots, or selection of sub-regions of the spectra for the successive measurement shots, or selection of the whole spectra for the successive measurement shots.

5. The method of claim 1, wherein said subjecting further comprises controlling operation of the laser and a plurality of said at least one spectrum detectors to simultaneously detect spectral emissions from the geological sample across a plurality of different spectral regions, and said analysing comprises determining the presence and amount of a plurality of different elements in the geological sample.

6. The method of claim 1, wherein the sample is a rock sample.

7. The method of claim 1, wherein each of the at least one spectrum detectors comprises a spectrometer having a CCD detector associated therewith.

8. The method of claim 1, further comprising:
(a) obtaining spatial information on the geological sample; and
(b) determining spatially resolved geochemical information for the geological sample using the geochemistry parameter and the spatial information.

9. The method of claim 1, wherein the preprocessing includes two or more of the integration of one or more peak areas to produce an intensity curve or curves, or selection of the actual peak spectra for successive measurement shots, or selection of sub-regions of the spectra for the successive measurement shots, or selection of the whole spectra for the successive measurement shots.

10. A system for analysing a geological sample, comprising:
i) a laser configured to subject at least one location of a geological sample to a plurality of successive measurement shots of laser light with each measurement shot at least partly vaporising and turning a portion of said geological sample into plasma to cause spectral emission;
ii) at least one spectrum detector configured to obtain spectral data on the geological sample by detecting said spectral emission after each said measurement shot;
iii) a controller for controlling the firing of the laser and for controlling and synchronising operation of the at least one spectrum detector therewith; and
iv) a computer configured to a) preprocess collected data from the at least one spectrum detector to form pre-processed data for analysis, wherein the preprocessing comprises integration of one or more peak areas to produce an intensity curve or curves, or selection of the actual peak spectra for successive measurement shots, or sub-regions of the spectra or the whole spectra for the successive measurement shots, and b) determine bitumen content of the geological sample, kerogen content of the geological sample, or both using the pre-processed data from the at least one spectrum detector.

11. A method for analysing a geological sample, comprising:
subjecting at least one location of a geological sample to a plurality of successive measurement shots of laser light from a laser with each measurement shot at least partly vaporising and turning a portion of said sample into plasma to cause spectral emission, wherein the geological sample contains organic matter;
detecting said spectral emission after each said measurement shot with at least one spectral detector;
preprocessing of collected spectral data from the at least one spectrum detector to form pre-processed data for analysis, wherein the preprocessing comprises one or more of:
integration of one or more peak areas to produce an intensity curve or curves, or
selection of the actual peak spectra for successive measurement shots, or
selection of sub-regions of the spectra for the successive measurement shots, or
selection of the whole spectra for the successive measurement shots; and
determining a reaction rate constant k for the Arrhenius equation of the at least one sample using the pre-processed data from the at least one spectrum detector.

12. The method of claim 11, wherein the determining of the reaction rate constant k using the pre-processed spectral data from the at least one spectral detector comprises at least one of:
i) determining changes in amounts of elements associated with organic matter and hydrocarbons for a portion of at least one sample that is heated by the laser-induced pyrolysis,
ii) analysing hydrocarbon species produced by pyrolysis of a portion of at least one sample from LIBS further by a flame ion detector or gas chromatography-mass spectrometry or by monitoring the weight of the sample during LIBS,
iii) monitoring the temperature of at least one sample and determining the amount of energy inputted into the portion of the sample by the laser during LIBS.

13. The method of claim 11, wherein a prefactor in the Arrhenius equation is inputted based on a priori knowledge or solved for based on measurements performed on two or more different heating rates of the sample.

14. The method of claim 13, wherein the different heating rates are obtained by one or more of different laser power, laser spot size or laser shot rate, or any combination thereof.

15. The method of claim 11, wherein the determined reaction rate constant k is used to either solve for the activation energy distribution in the sample or the reaction rates given a known input of energy.

16. The method of claim 11, wherein the geological sample comprises heterogeneous rock comprising different kinds of organic matter.

17. The method of claim 11, wherein the geological sample comprises heterogeneous rock comprising kerogen and bitumen.

* * * * *